United States Patent [19]

Hertzmann et al.

[11] Patent Number: 5,084,043

[45] Date of Patent: Jan. 28, 1992

[54] METHOD FOR PERFORMING A PERCUTANEOUS DISKECTOMY USING A LASER

[75] Inventors: Peter S. Hertzmann, Palo Alto, Calif.; Jordan K. Davis, Boca Raton, Fla.

[73] Assignee: Laserscope, San Jose, Calif.

[21] Appl. No.: 463,759

[22] Filed: Jan. 12, 1990

[51] Int. Cl.$^5$ .............................................. A61N 5/06
[52] U.S. Cl. ........................................ 606/3; 606/13; 606/18; 128/395; 128/397
[58] Field of Search ............... 128/395, 397, 398, 898, 128/897; 606/3, 13-19

[56] References Cited

U.S. PATENT DOCUMENTS

| | | | |
|---|---|---|---|
| 3,769,963 | 11/1973 | Goldman et al. | 128/395 |
| 4,369,788 | 1/1983 | Goald | 128/751 |
| 4,545,374 | 10/1985 | Jacobsen | 604/164 |
| 4,678,459 | 7/1987 | Onik et al. | 604/22 |
| 4,694,828 | 1/1987 | Eichenbaum | 606/4 |
| 4,737,628 | 4/1988 | Lovoi | 128/395 |

OTHER PUBLICATIONS

Dorlands Illustrated Medical Dictionary; W. B. Saunders Philadelphia, London, Toronto, p. 465.

"Ultraviolet Laser Ablation of Skin", by Lane et al., Arch of Derm. 784.

"Effect of Laser on Human Vertibral Disc at Excimer Argon, ND:VAG(1.06, 1.32 nm), 2.0, 2.92 and $CO_2$ Frequencies", by Choy et al., Abst. #201, p. 48; Lasers in Surg. & Med. Supp I, 489.

Hijikata S., Yamagishi M., Nakayama T., Oomori K., "Percutaneous Diskectomy: A New Treatment for Lumbar Disc Herniation", J. Toden Hosp., 1975; 5:5-13, Copy not available.

Ascher P. W., Choy, D. S., Yuri H., "Percutaneous Nucleus Pulposus Denaturation and Vaporization of Protruded Discs", Abstract #202, p. 48, Lasers in Surgery and Medicine, Supplement 1, 1989.

Ascher P. W., "Laser Trends in Minimally Invasive Treatment, Atherosclerosis, Disc Herniations", Section 2, presented at the Biomedical Optics Conference of SPIE, Los Angeles, Jan. 26, 1990.

*Primary Examiner*—David Shay
*Attorney, Agent, or Firm*—Davis, Paul

[57] ABSTRACT

A method for performing percutaneous diskectomy using a laser applies a laser beam from the laser to vaporize nucleus pulposus in the nucleus of the herniated disc. The wavelength of the laser beam will vary and depend on the laser system used.

29 Claims, 21 Drawing Sheets

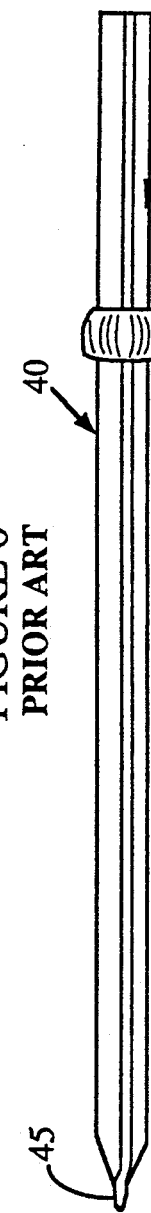
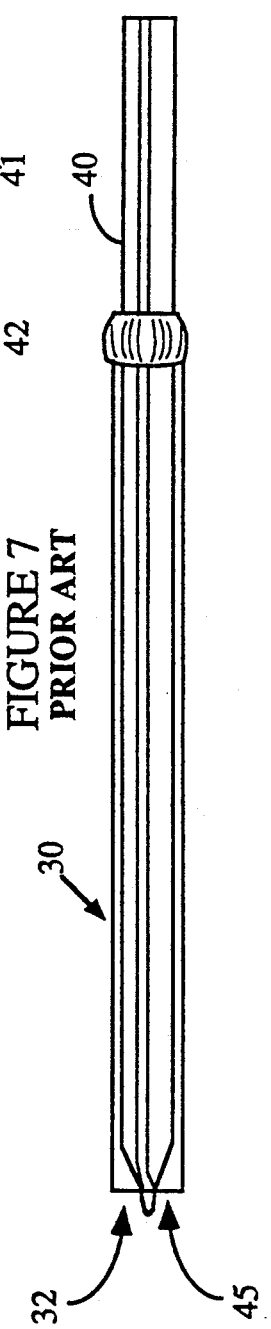
FIGURE 6 PRIOR ART
FIGURE 7 PRIOR ART
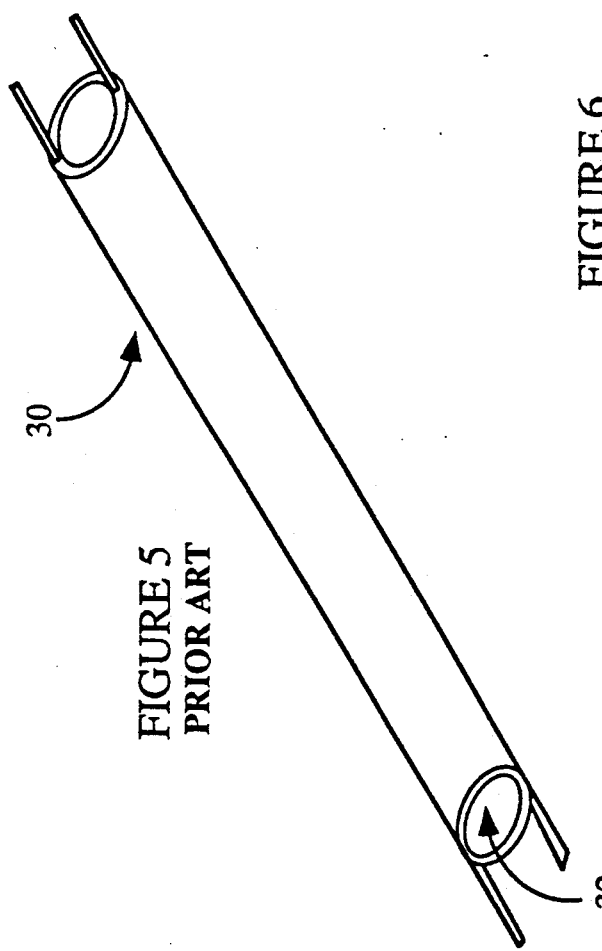
FIGURE 5 PRIOR ART
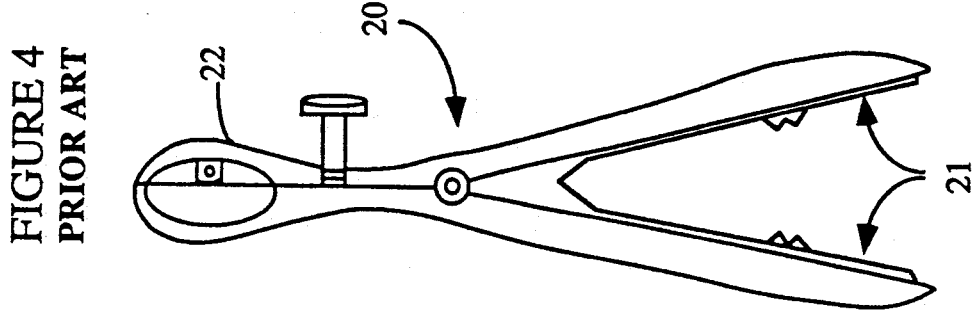
FIGURE 4 PRIOR ART

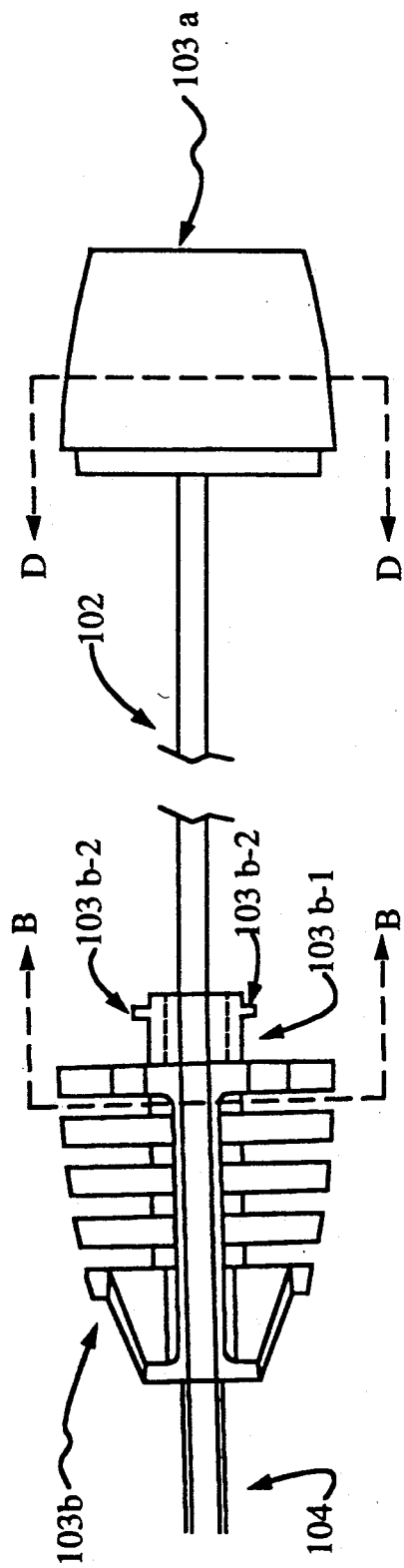
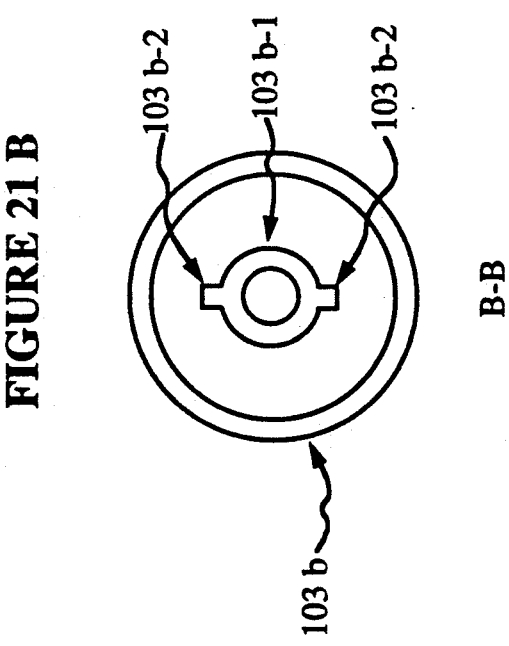
FIGURE 21 A
FIGURE 21 B
FIGURE 21 C
FIGURE 21 D

F-F

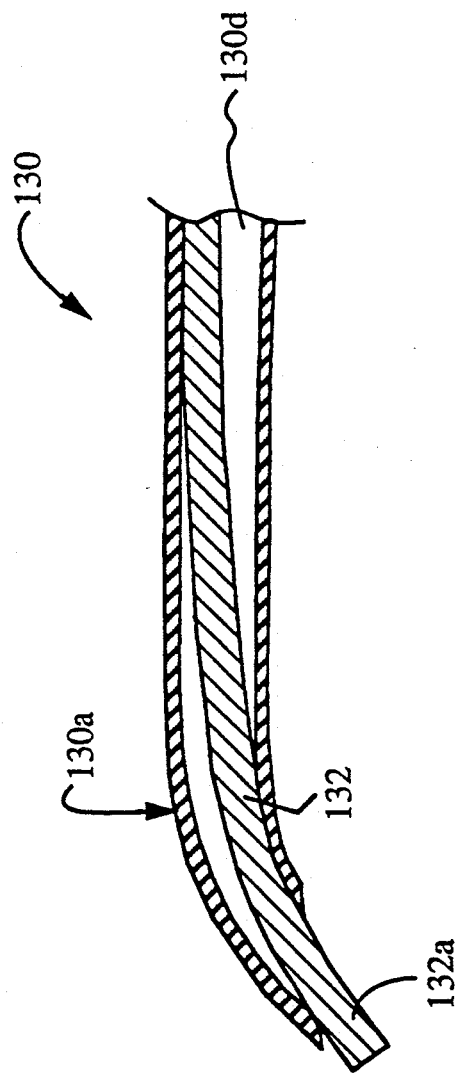
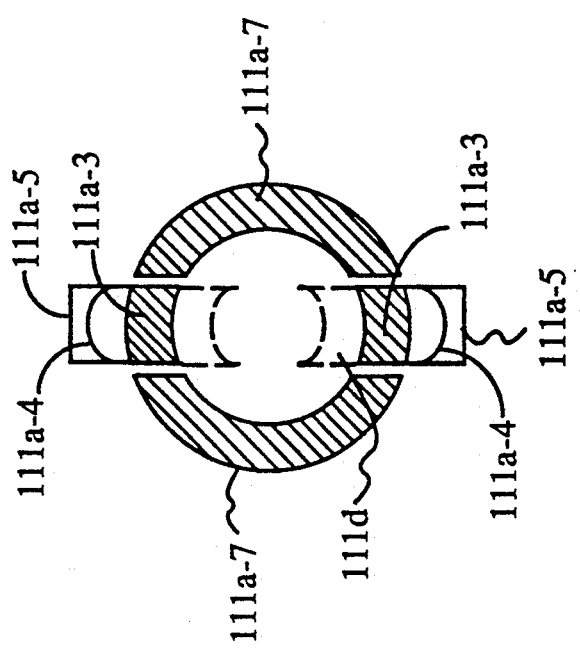
FIGURE 27
FIGURE 25B
SECTION B-B

SECTION F-F

END VIEW

METHOD FOR PERFORMING A PERCUTANEOUS DISKECTOMY USING A LASER

BACKGROUND OF THE INVENTION

1. Field of the Invention

This invention relates to a method for vaporizing nucleus pulposus within a lumbar disc of the vertebral column during a percutaneous diskectomy procedure using a laser.

2. Description of the Prior Art

Mechanically assisted percutaneous lumbar diskectomy of the prior art is used as a treatment of leg pain (sciatica) resulting from herniated discs of the lumbar vertebral column. The lumbar vertebral column consists of five vertebrae extending superiorly to the transitional thoracic vertebrae (1) at a first end and extending inferiorally to the sacrum (3) at a second end, as illustrated in FIG. 1. Between each lumbar vertebrae and between the lumbar and sacrum are cartilaginous discs. Each disc comprises an outer circular structure (annulus fibrosus) 2 which surrounds and tightly binds an inner gelatinous material (nucleus pulposus) 4 in the center, as illustrated in FIG. 2. The annulus fibrosus 2 is made up of concentric fiberts which appear to cross each other obliquely. No blood vessels or nerves penetrate the nucleus.

Usually with age, the fibers of the annulus begin to degenerate. The degeneration results in the tearing of individual fibers when the vertebral column is stressed. Torn fibers can form fenestrations which allow the nucleus pulposus to move through the fibers of the annulus and bulge 5 outward away from the nucleus. If the bulged disc presses upon an adjacent nerve root 6, sciatica may develop, as illustrated in FIG. 3A.

It has been demonstrated that removing a portion of the nucleus with grasping forceps through a small cannula will produce good to excellent relief of pain in a majority of patients having symptoms indicative of sciatica. Once a portion of the nucleus is removed, the pressure against the nerve root causing the pain is relieved as the remaining nucleus contracts away from the pressure point, as illustrated in FIG. 3B. Hijikata S., Yamagishi M., Nakayama T., Oomori K., "Percutaneous Diskectomy: A New Treatment for Lumbar Disc Herniation", J. Toden Hospital 1975; 5:5-13. Since the Hijikata et al. article, mechanical forceps for microlumbar and percutaneous lumbar diskectomy procedures have been developed related to relieving sciatica pain.

U.S. Pat. No. 4,369,788, which issued in Jan. 25, 1983 to Goald teaches one such forceps device having an alligator jaw for microlumbar disc surgery. The forceps can be held by a surgeon in a reversed backhand grip which aids in their manipulation during microlumbar disc surgery procedures. For microlumbar disc surgery, a one-inch incision is made in the patient into which the forceps are inserted and the surgery is performed.

U.S. Pat. No. 4,545,374, which issued on Oct. 8, 1985 to Jacobson teaches a method and instruments for performing percutaneous diskectomy. The instrumentation taught by Jacobson is illustrated in FIGS. 4-10 and includes a speculum 20 which has a pair of semi-sharp edged blades 21 for piercing and stretching body tissue and pivotally hinged handles 22 for opening and closing the blades, as illustrated in FIG. 4. Speculum 20 has a guide means for guiding the speculum along a slender member such as a spinal needle (not shown) having a diameter of less than 3 millimeters. The guide means can be any form of a bore or hole through which the spinal needle can pass. Jacobson also teaches a cannula 30, which is illustrated in FIG. 5. Cannula 30 is a cylindrical tool having a bore 32 for passing instruments therethrough from outside the body to inside the body. Cannula 30 has an oval cross section for allowing different sized and shaped instruments therethrough. Cannula 30 also has anchor means for anchoring the cannula to the disc. Jacobson teaches using a trocar 40 which is inserted into cannula 30, as illustrated in FIGS. 6 and 7. Trocar 40 has a shaft 41 and a collar 42. Shaft 41 fits into hole 32 of cannula 30 to a point where collar 42 is located. Collar 42 is adjustable, thereby allowing shaft 41 to be adjustably inserted at different lengths into hole 32. Shaft 41 of trocar 40 is tapered at one end to a point 45 for anchoring into body tissue. A knife 50, as illustrated in FIG. 8, having a blade end 53, 54 and a handle 51 at an opposite end to the blade end is insertable through cannula 30. Blade end 53, 54 is curved to allow quick and more efficient fragmentation of disc nucleus pulposus because it undergoes a curved cutting path during use. Rongeur forceps 60 for removing fragmented disc nucleus material are inserted into the cannula after knife 50 is removed. Rongeur forceps 60 have scissor-like handles 61, 62 pivotally connected near one end by pivot 63 and a jaw 68, 69, wherein spreading the handles 61, 62 opens the jaw 68, 69 and squeezing the handles 61, 62 closes the jaw 68, 69, as illustrated in FIG. 9.

The percutaneous lumbar diskectomy procedure taught by Jacobson includes placing a patient in a lateral decubitus position on an operating table; anesthetizing the patient usually with a long spinal needle which is guided into the disc area with the aid of fluoroscopic x-ray; incising a 1 centimeter long skin incision to create a percutaneous channel 9 with a speculum 20, as illustrated in FIG. 10. Speculum 20 is constructed to open and close and has jaw blades with semi sharp edges which spread rather than cut body tissue. Guiding speculum 20 by guide means over spinal needle 24 until properly located; spreading the jaws of speculum 20 open to create channel 9 for the insertion of cannula 30 to act as a conduit for the insertion of tools; inserting cannula 30 with the aid of a trocar 40 and removing speculum 20. Trocar 40 adds stiffness to the flexible cannula and eases its insertion along with the guidance of fluoroscopic x-ray. Trocar 40 can have pointed tip 45 which sticks into the disc capsule 8 and prevents lateral movement of cannula 30. Passing a nerve stimulator 80 (not shown) down channel 9 with cannula 30 or trocar 40. Stimulator 80 will cause motion in one of the patient's legs if it makes nerve contact, thereby signaling the surgeon that a slightly different insertion position is necessary. Cutting a hole in the annulus fibrosus surrounding the nucleus with knife 50 or another trocar having a rotatable reamer; fragmenting the nucleus pulposus with knife 50, ultrasonics, laser or dissolving chemicals; removing fragments of nucleus pulposus with Rongeur forceps 60 and/or suction. Rongeur forceps 60 preferably have large angled jaws which sweep a wide arc and several Rongeur forceps may be used each with slightly different angled jaws to remove nucleus pulposus from different portions of the disc. The surgeon uses rotational motion about an axis defined by the shaft of the forceps in order to scoop out material about an axis of revolution. A Z-head Rongeur forceps can create a cavity of revolution by removing a large amount of nucleus material upon rotation. Flushing the cavity created in the nucleus pulposus with saline solution to clean out the space; suctioning out the solution and any debris contained therein; removing the cannula and stitching up the fat and fascia underneath the skin; and bandaging the outer skin surface with an adhesive strip to prevent suture scars.

Jacobson taught that this procedure requires one to two days recovery time, that outpatient convalescence is possible and that the total procedure time is approximately 15 minutes. Nevertheless, the instrumentation and procedure require extensive manipulation of tools by the surgeon, that a more streamlined procedure using fewer tools would be desirable. In practice, the Jacobson procedure has a 60% failure rate in relieving back pain and takes greater than 15 minutes to perform.

U.S. Pat. No. 4,678,459 issued to Onik et al. on July 7, 1987 teaches using an irrigating, cutting and aspirating system for percutaneous surgery. Onik et al. teaches using a system for removing nucleus pulposus tissue 79 which includes a probe and a guillotine type of cutting means 78 for cutting the nucleus pulposus 79, as illustrated in FIG. 11. The severed or cut fragments of nucleus pulposus 79 are removed from the cutting means 78 using an internal fluid irrigation system and a vacuum to aspirate the severed fragments out of the disc area, through the system, and out of the patient. This system provides for a relatively fast diskectomy procedure compared to the other prior art because nucleus pulposus can be fragmented and removed without the need to manipulate many small blades, knives and forceps, as described for the Jacobsen U.S. Pat. No. 4,545,374. The probe and guillotine-type cutting means taught by Onik et al. is sold on the market as a Nucleotome Probe 70, as illustrated in FIG. 15. This instrument is the most widely used instrument for percutaneous diskectomy. The procedure and instrumentation used to implement the Nucleotome Probe 70 include placement of a FlexTrocar 71 into a 3 millimeter skin incision made on the side of the patient's body where the herniation is evident. The FlexTrocar 71 is inserted until it contacts the annulus fibrosus 72 of the herniated disc, as illustrated in FIG. 12, using the guidance of a fluoroscopic X-ray. Once the FlexTrocar 71 is in place, a straight cannula 73 having a tapered dilator 74 is passed over the FlexTrocar 71 and inserted down to the annulus 72 wall, as illustrated in FIG. 13. The position of the straight cannula 73 is confirmed fluoroscopically. Once the cannula 73 is in place, the tapered dilator 74 is removed from the cannula 73. A trephine 75 is inserted through the cannula 73 and over the FlexTrocar 71. The trephine 75 is rotated in a clockwise motion with slight pressure to incise the annulus, as illustrated in FIG. 14. The trephine 75 and the FlexTrocar 71 are subsequently removed from the patient's body. The Nucleotome Probe 70 is inserted into the cannula 73 after the trephine 75 and FlexTrocar 71 are removed. The Nucleotome Probe 70 locks into place on the cannula 73, as illustrated in FIG. 15. When the Nucleotome Probe 70 is activated, the nucleus pulposus is cut into fragments which are removed with irrigation fluids and suction, all within the Nucleotome Probe 70. The Nucleotome Probe 70 is activated until no further material can be extracted. Once complete, the Nucleotome Probe 70 and cannula 73 are removed and the entry point is covered with a sterile bandage. The cutting and extracting process alone using the Nucleotome Probe 70 normally takes between 20 to 30 minutes.

In 1989, P. W. Ascher, D. S. Choy and H. Yuri suggested using lasers to vaporize disc material in a percutaneous diskectomy procedure. Ascher et al. believed the $CO_2$ laser was not a viable choice for percutaneous diskectomy because an optical fiber for the $CO_2$ laser was not yet available. Ascher et al. reported using an Nd:YAG laser at 1060 nm since an optical fiber was available. Ascher et al. were aware that the Nd:YAG laser at 1060 nm had low absorption in water and white tissue and high absorptivity in water and white tissue is necessary to produce effective vaporization of nucleus pulposus. Tests were performed with less than encouraging results. Also, Ascher et al. reported using a Nd:YAG laser at 1320 nm and claimed it produced twice as much volume reduction as compared to the 1060 nm laser. Nevertheless, Ascher et al. reported that only the $CO_2$ laser, or the Er:YAG laser would produce sufficient results in about 10–15% of patients having the requisite symptoms. Abstract No. 202, p. 48, entitled "Percutaneous Nucleus Pulposus Denaturization and Vaporization of Protruded Discs", American Society for Laser Medicine and Surgery: Lasers in Surgery and Medicine, Supplement 1, 1989.

The results of the Ascher et al. investigations did not produce safe and effective results using a laser to vaporize nucleus pulposus from herniated discs. It would be desirable if a laser technique and laser instrumentation were available to perform percutaneous diskectomies so that nucleus pulposus from herniated discs could be vaporized using a laser in a safe and effective way which is faster than cutting and irrigating using the Nucleotome Probe and which would eliminate the need to cut and remove fragmented debris from the patient.

SUMMARY OF THE INVENTION

Therefore it is an object of the present invention to provide a method for performing percutaneous diskectomy using a laser in a safe and effective manner.

According to the object of the present invention a method for performing percutaneous diskectomy using a laser comprises applying a laser beam from the laser to a herniated disc area, the laser beam having a wavelength in the range of 350 through 1000 nm. The wavelength of the laser beam applied to the herniated disc according to the present invention will vary and depend on the laser system used.

A safe manner of performing a percutaneous diskectomy using a laser is defined as using a laser system which vaporizes the target material with minimal thermal damage to adjacent structures. An effective manner of performing a percutaneous diskectomy using a laser is defined as using a laser system which sufficiently vaporizes the target material to relieve the pain at least caused by sciatica.

BRIEF DESCRIPTION OF THE DRAWINGS

FIG. 4 is a side view of a prior art speculum.

FIG. 5 is a oblique view of a prior art cannula.

FIG. 6 is a side view of a probe of the prior art.

FIG. 7 is a side view of the probe in FIG. 6 inserted into the cannula of FIG. 5.

FIG. 27 is an exploded sectional view illustrating an optical guiding means emanating from the formed end of introducer means according to the present invention.

DETAILED DESCRIPTION OF THE INVENTION

A percutaneous diskectomy procedure using a laser is designed for patients commonly showing evidence clinically and radiologically of nerve root impingement. Conventionally, physical examination of the patient should reveal leg pain greater than back pain and signs of nerve root irritation consistent with a herniated disc. Radiographically, the patient should exhibit a focal herniation or bulge that shows an impression on the thecal sac which does not occupy more than fifty percent of the thecal sac. Also, the radiographic results should correlate with the patient's symptomatology.

Vaporization of nucleus pulposus material according to the present invention suggests that the operative tools be inserted at an entry site on the same side of the patient's body that the herniation or other affliction is evident. The path of entry to the afflicted disc should avoid going through the psoas muscle since the lumbar plexus has numerous fibers which traverse the muscle. Conventionally, a computed tomograph (CT) scan slice of the whole abdomen through the involved disc is quite helpful for determining the entry path.

The safety of the procedure relies on radiologic localization and guidance of the instruments into the disc and a C-arm fluoroscope with image intensification, known in the art, can provide clear and sharp images in anteroposterior, lateral and oblique views.

Figure 16:
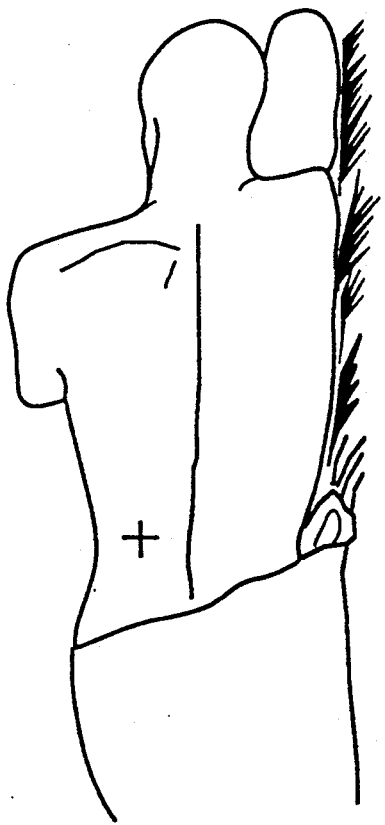
FIG. 16 is a posterior view of a patient in a lateral decubitus position.

Typically, the patient undergoing a percutaneous diskectomy procedure is positioned on a fluoroscopic table, which is known in the art, in a lateral decubitus position, as illustrated in FIG. 16. The patient must be stabilized to prevent rotation of the patient's shoulders and hips during the procedure. Using a fluoroscope, the sacrum is identified and located, the afflicted disc is located, and as illustrated in FIG. 16, a posterolateral entry point is selected. The entry point typically is 8-12 centimeters from the midline and both parallel and midway between the end plates of the afflicted disc, as determined using a measuring scale. Local anesthetic is used to anesthetize the area to be operated on which is administered typically with a long spinal needle.

At this point in the patient preparation procedure, the percutaneous diskectomy procedure using a laser and means for inserting instrumentation according to the present invention is described.

Figure 17:
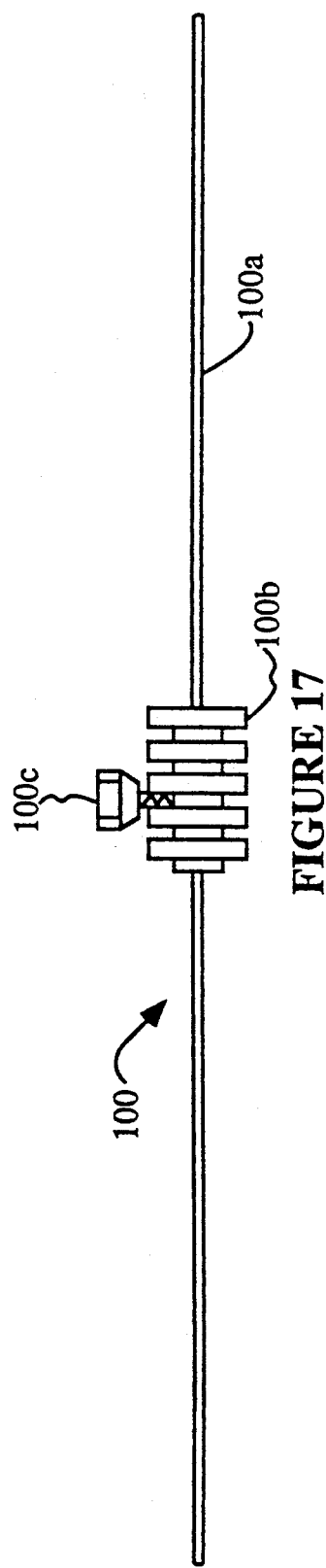
FIG. 17 is a side view illustrating a probe used with the present invention.

First, one end of a semi-rigid trocar or probe 100, which is preferably 18 gauge Birmingham Wire Gauge (BWG), is inserted at the entry point once the anesthetic has taken effect. Probe 100 has an elongated body 100a and has a standard tube clamp 100b with a threaded lock 100c connected 26 to probe 100, as illustrated in FIG. 17.

Clamp 100b is removable from body 100a by loosening lock 100c and sliding clamp 100b in either direction beyond the end of probe 100. Clamp 100b serves as a handle to hold probe 100 while it is inserted into the patient. Clamp 100b is removed for subsequent steps described below. Clamp 100b may be made of plastic, for example acrylonitrile-butadiene-styrene (ABS) plastic or preferably polycarbonate plastic, or metal, preferably stainless steel.

Figure 18:
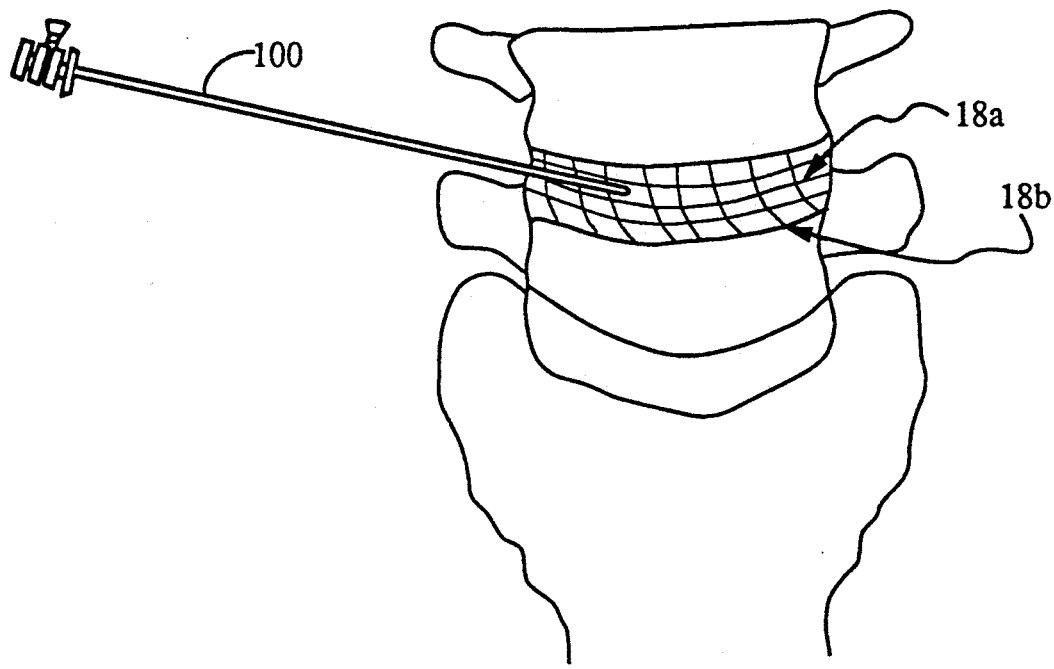
FIG. 18 is an oblique view illustrating the probe inserted into a disc according to the present invention.
Figure 19:
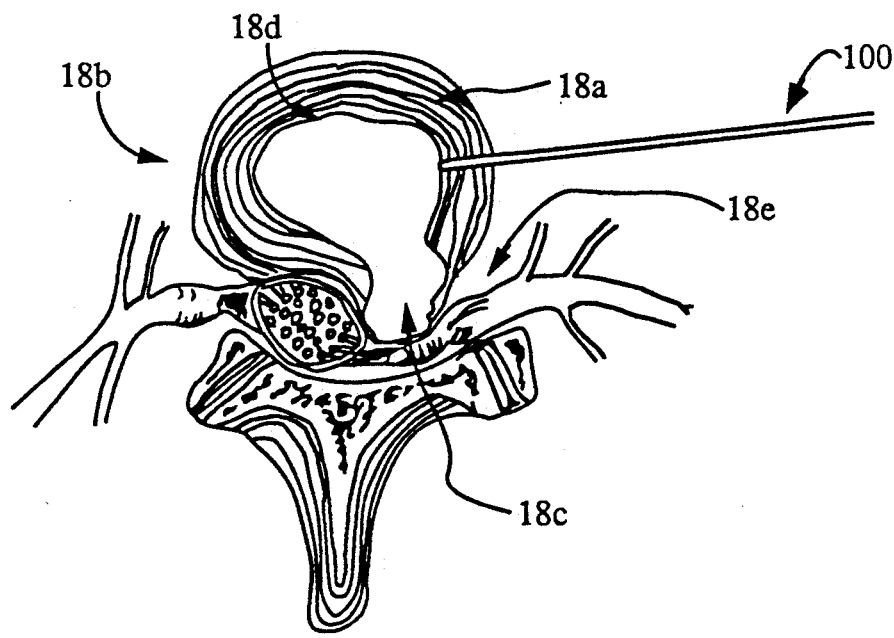
FIG. 19 is a sectional view of a herniated disc and associated nerve root having the probe inserted thereinto according to the present invention.
Figure 21:
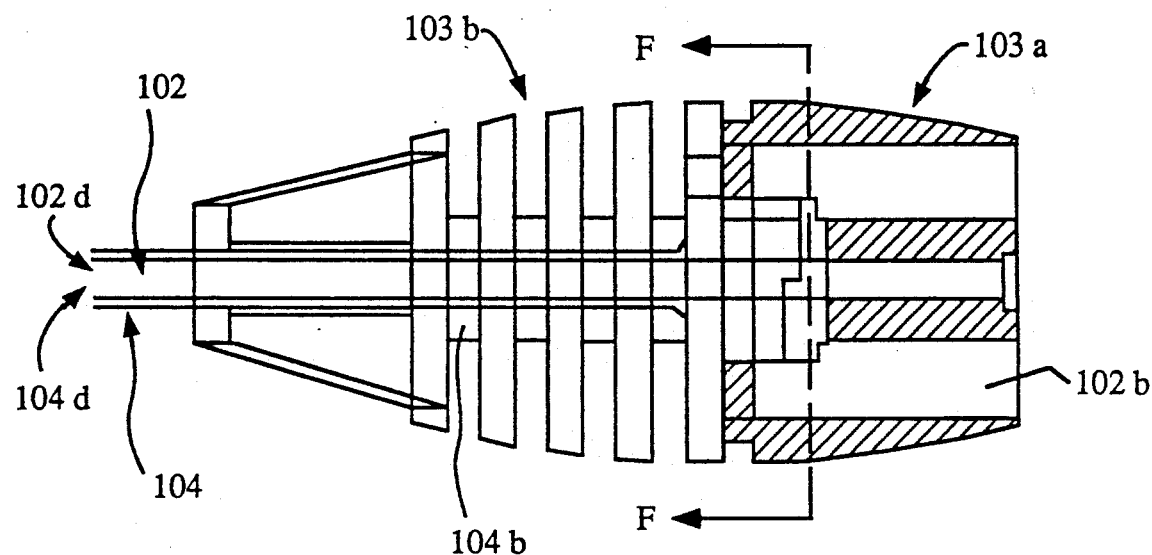
FIGS. 21A-21E are sectional and plan views of a bayonet type lock fitting used with the present invention.
Figure 21:
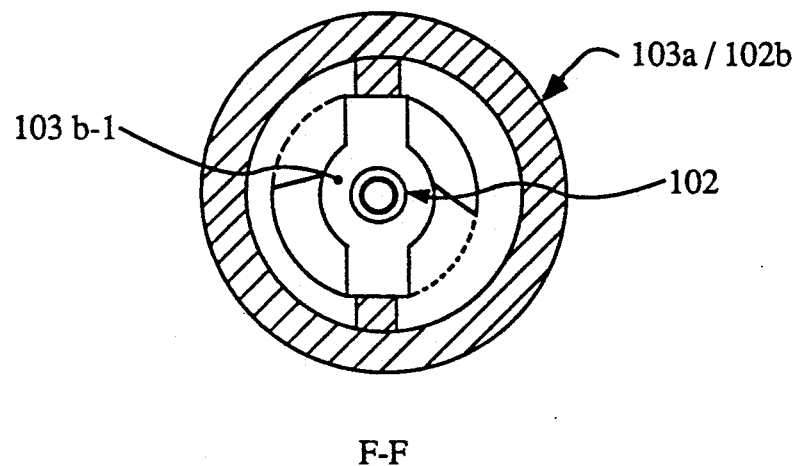

Probe 100 is preferably made of stainless steel also, for example type 304 or an equivalent, No. 3 temper. The inserted end of probe 100 has a sharp tip and is guided into the damaged or herniated disc area 18c with radiologic localization and guidance, preferably using the C-arm fluoroscope with image intensification, as described above. Probe 100 is inserted until the inserted end punctures through the annulus fibrosus 18a of the disc 18b, as illustrated in FIGS. 18 and 19. While probe 100 is in place, extending from the disc area to outside the patient's body, a cannula 104 having a dilator 102 inserted thereinto is inserted over probe 100 at the exterior end and into the probed disc area 18c. One end of dilator 102 (102b) and cannula 104 (104b) remain on the exterior of the patient.

Figure 20:
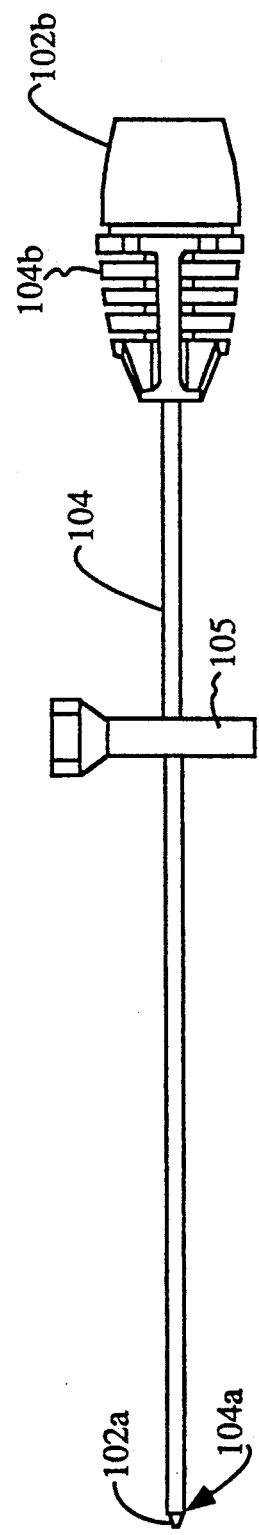
FIG. 20 is a side view of a cannula having a dilator inserted thereinto used with the present invention.

Cannula 104 and dilator 102 are preferably 12 gauge stainless steel tubing, for example type 304, No. 3 temper (full hard). Stainless steel tubing may be purchased at any stainless steel tubing supplier, for example Poper and Sons, N.Y. Dilator 102 preferably is longer than cannula 104 and has a tapered end 102a which extends beyond the end 104a of cannula 104, as illustrated in FIG. 20, for ease of insertion over probe 100 through the patient's skin. Dilator 102 has bore 102d which extends through the center of dilator 102 along its length. Probe 100 fits within bore 102d of dilator 102. Cannula 104 is preferably a straight tubular member having a central bore 104d, which extends along its length. Dilator 102 and probe 100 fit within bore 104d of cannula 104.

Cannula 104 and dilator 102 have locking means 103 (103 mechanism not shown) for locking dilator 102 to cannula 104 at end 104b and 102b, respectively, and a locking stabilizer 105, as illustrated in FIG. 20. Locking means 103 is preferably a bayonet-fitting locking mechanism, as illustrated in FIGS. 21A-21F. Dilator 102 has portion 103a and cannula 104 has portion 103b of bayonet-fitting locking mechanism 103. Portion 103b on cannula 104 has a segmented body and flared legs for gripping and preferably projection 103b-1 having two laterally extending flanges 103b-2 which oppose one another. Portion 103a on dilator 102 preferably has aperture 103a-1 and sockets 103a-2. Aperture 103a-1 is at least as deep as the distance projection 103b-1 projects. Sockets 103a-2 oppositely extend off aperture 103a-1 and are at least as deep as flanges 103b-2 are thick. Projection 103b-1 and flanges 103b-2 fit within aperture 103a-1 and sockets 103a-2, respectively. Once fitted together, end 102b of dilator 102 is turned clockwise thereby rotating dilator 102 within cannula 104 to lock locking portion 103a to locking portion 103b and thereby lock dilator 102 to cannula 104 using locking means 103. Locking means 103 can also be a luer lock, threaded screw lock, snap lock or a friction fitted lock, which are known in the art. Locking means 103, and stabilizer 105 can be made of plastic, ABS or preferably polycarbonate plastic, or metal, preferably stainless steel. In the preferred embodiment, means 103, ends and stabilizer 105 are made of a plastic which can withstand at least the stresses associated with gamma sterilization techniques without distortion. The plastic may also withstand the stresses associated with autoclaving and usage of ethylene oxide gas sterilization methods. Locking stabilizer 105 is adjustably located along the length of cannula 104 and serves to rest against the patient's skin when the cannula is properly placed.

Figure 2:
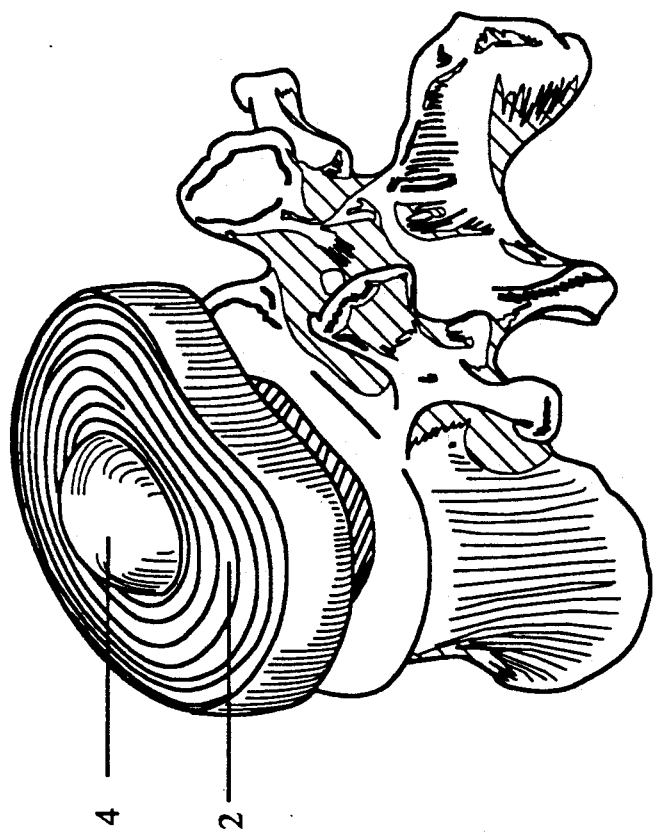
FIG. 2 is an oblique view of a lumbar disc and inferior vertebrae.
Figure 1:
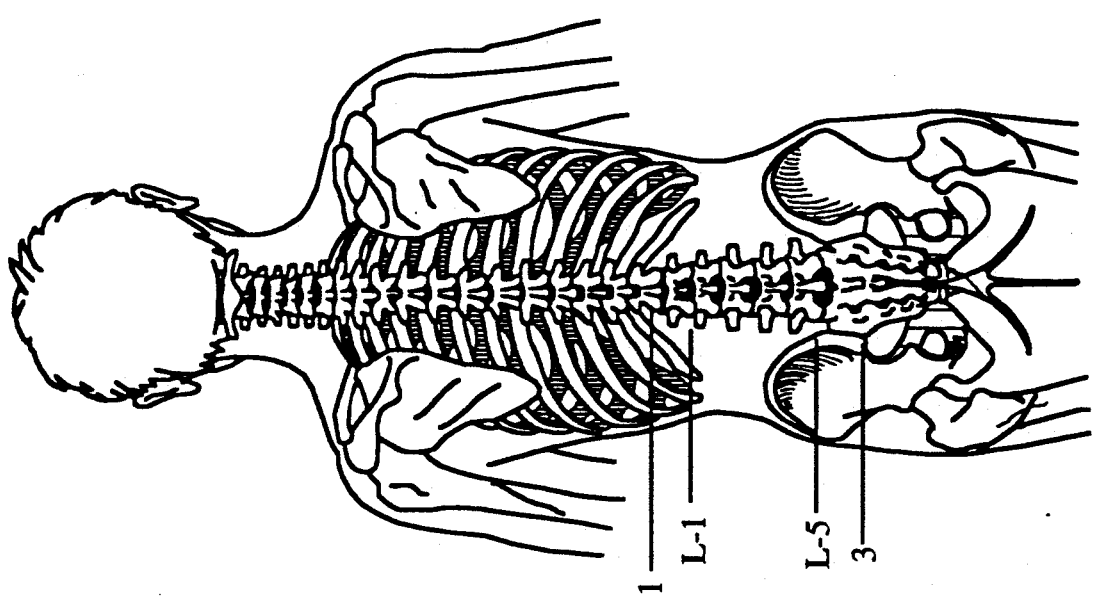
FIG. 1 is a posterior view of the lumbar vertebral column.
Figure 3B:
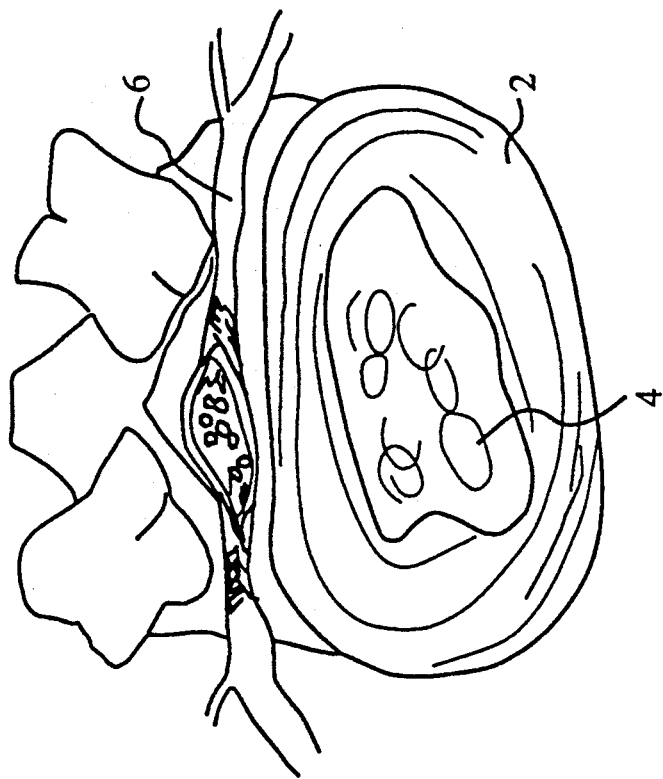
FIG. 3B is a sectional view of the vertebrae in FIG. 3A after nucleus pulposus is removed.
Figure 3A:
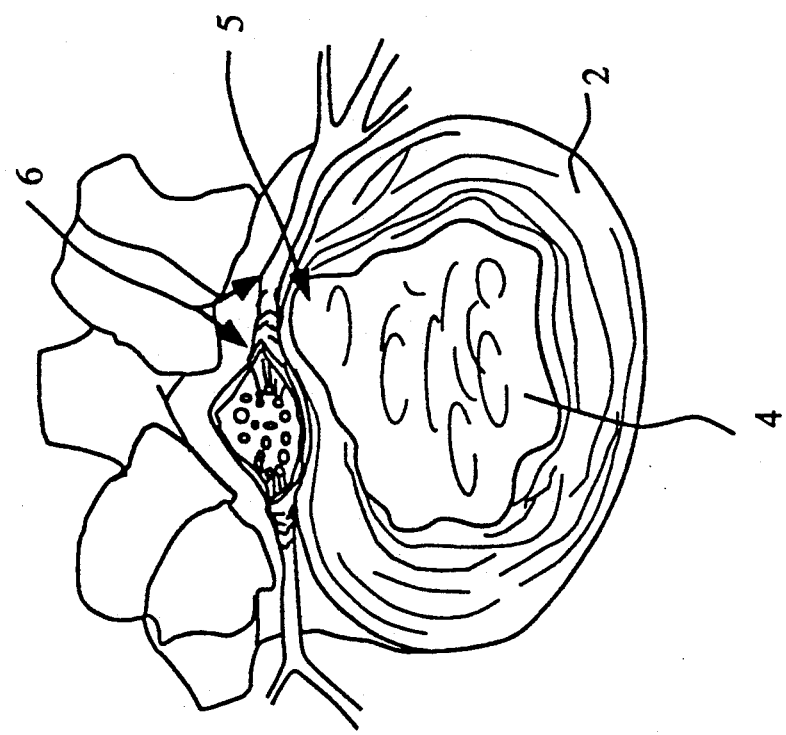
FIG. 3A is a sectional view of a herniated lumbar vertebrae and an associated nerve root.
Figure 8:
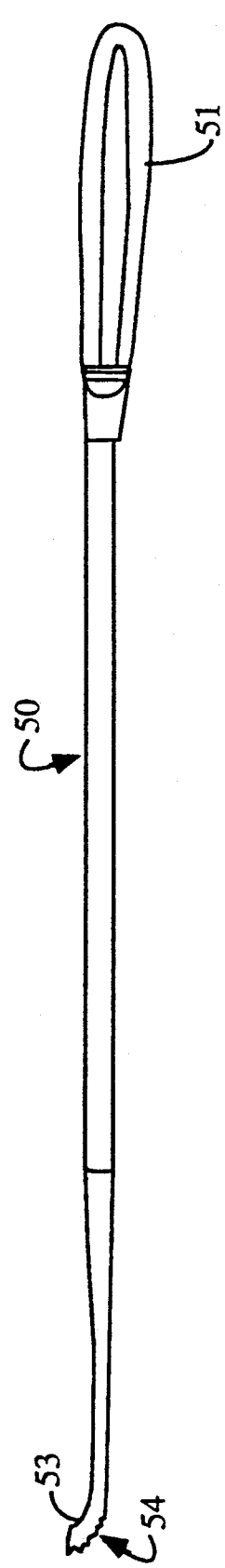
FIG. 8 is a side view of a knife of the prior art.
Figure 9:
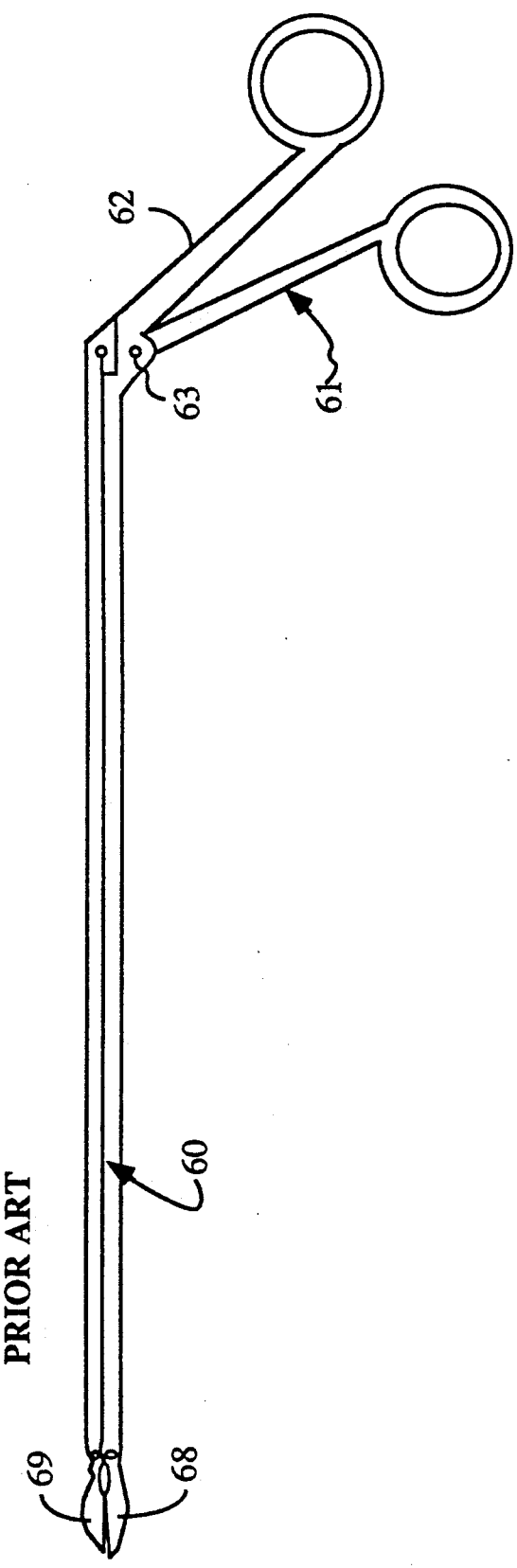
FIG. 9 is a side view of a prior art Rongeur forceps.
Figure 10:
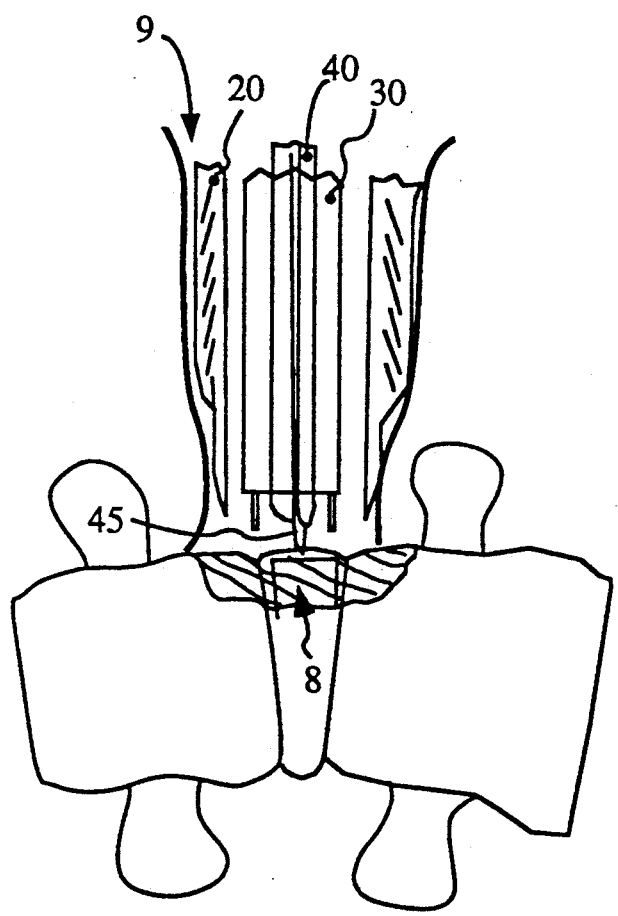
FIG. 10 is a sectional view of a channel created by the prior art speculum in FIG. 4.
Figures 11, 12:
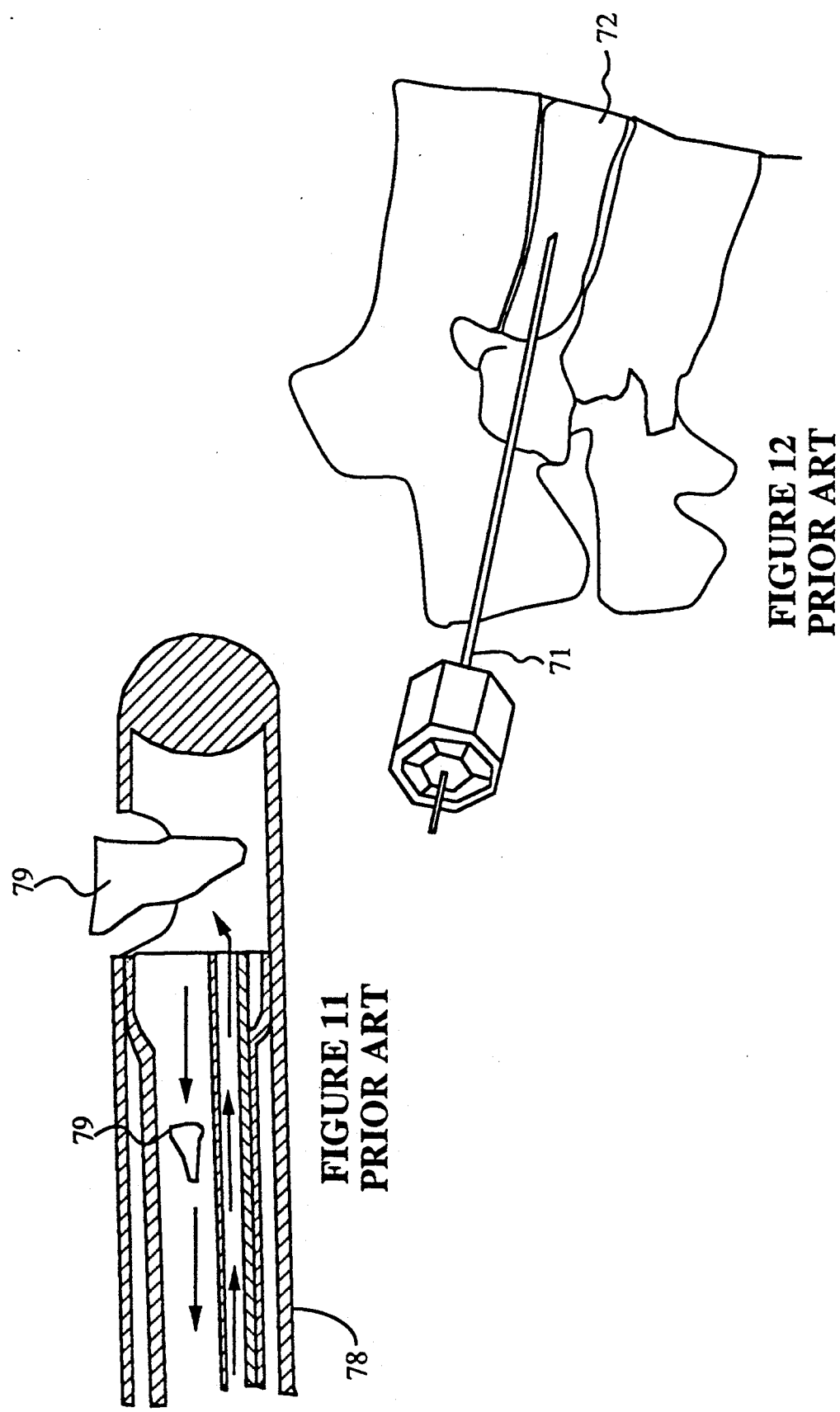
FIG. 11 is an exploded sectional view of the Nucleotome Probe of the prior art.
FIG. 12 is an oblique view illustrating FlexTrocar of the prior art entering the disc area.
Figure 13:
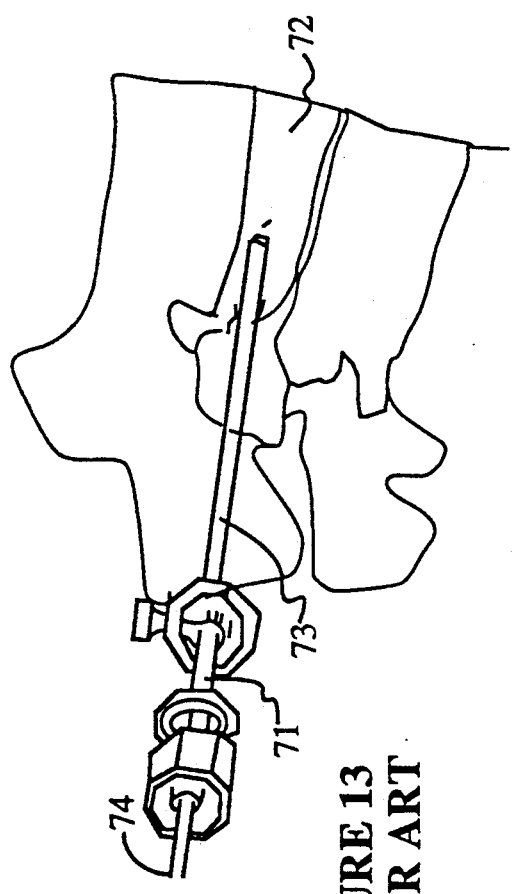
FIG. 13 is an oblique view illustrating straight cannula and tapered dilator of the prior art.
Figure 14:
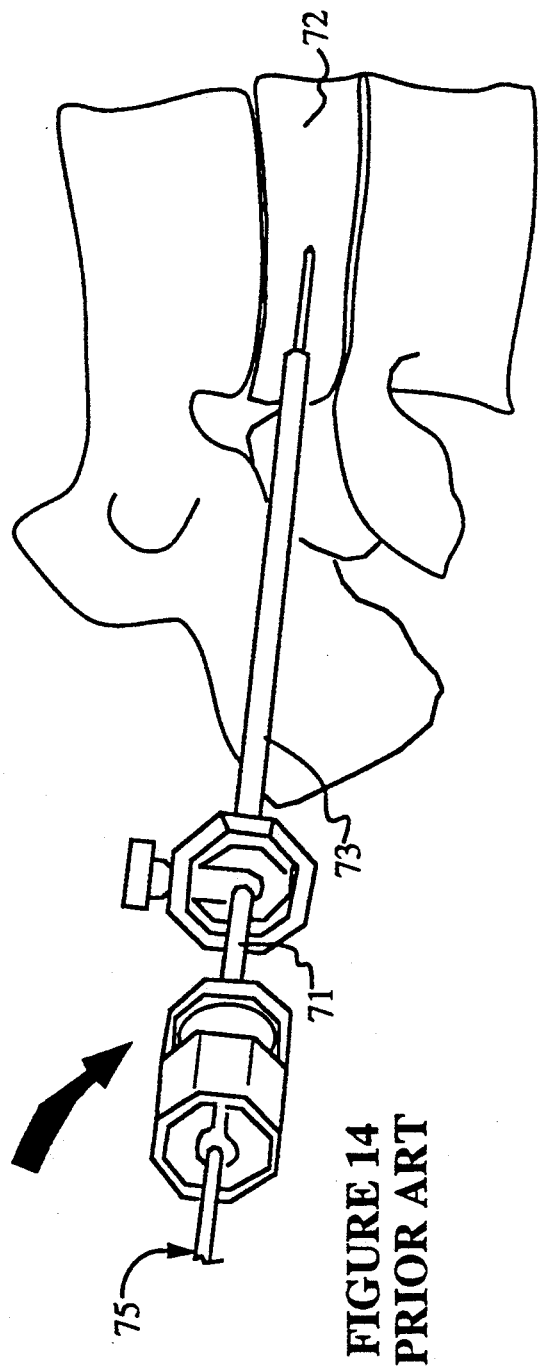
FIG. 14 is an oblique view illustrating the trephine of the prior art.
Figure 15:
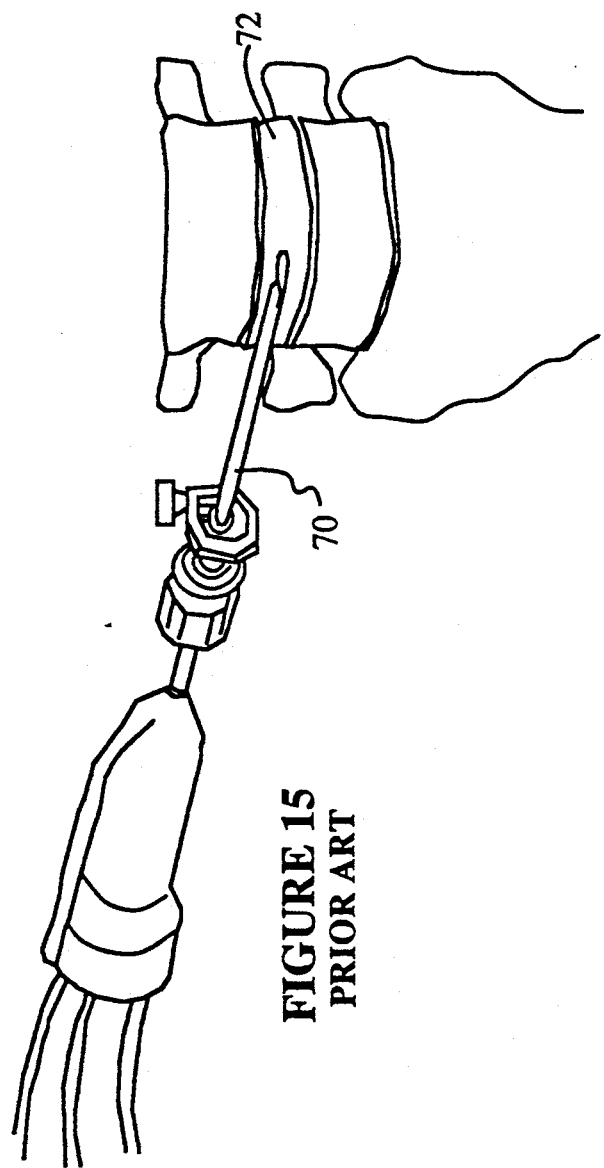
FIG. 15 is an oblique view illustrating the Nucleotome Probe of the prior art.
Figure 22:
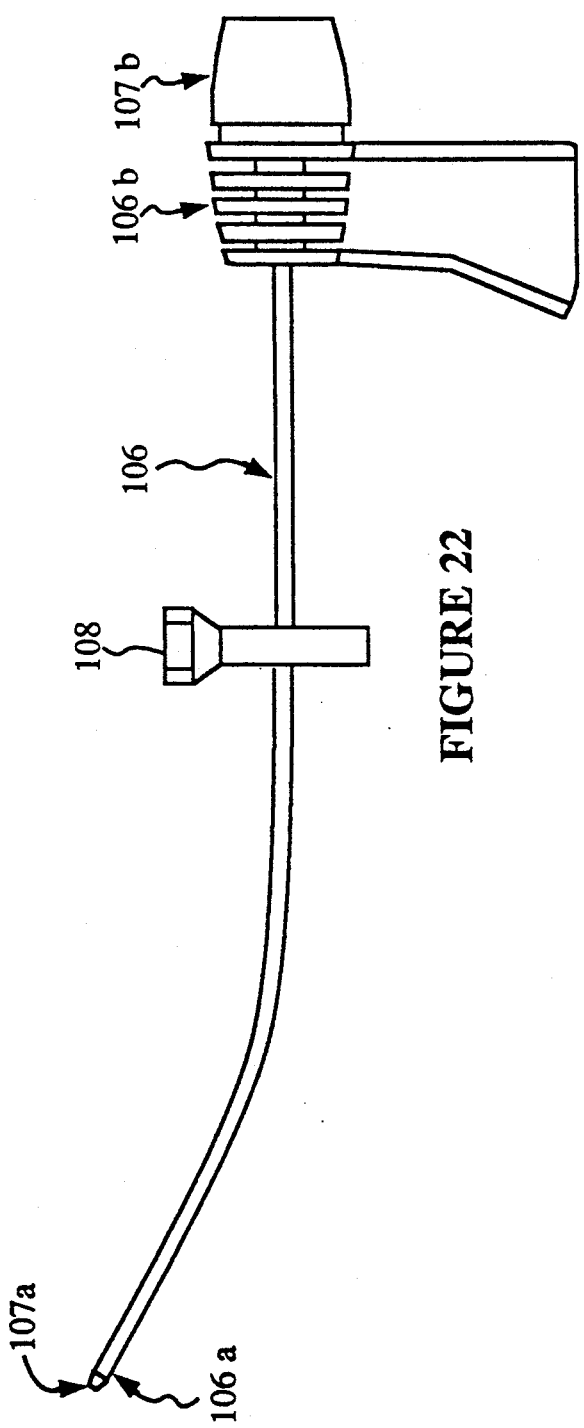
FIG. 22 is a side view illustrating a curved cannula used with the present invention.

In another embodiment, curved cannula 106 may be inserted into the patient instead of straight cannula 104. Cannula 106 is a curved tubular member having a locking dilator 107 and locking stabilizer 108, as illustrated in FIG. 22. Curved cannula 106 is used in situations where the patient's afflicted area is within the lumbar 5-sacrum 1 region of the vertebral column, as shown in FIG. 1.

Once dilator 102 and cannula 104 are confirmed, preferably fluoroscopically, to be embedded in the annulus fibrosus, dilator 102 is unlocked from locking mechanism 103 and removed. Dilator 102 is unlocked by turning portion 103a counterclockwise while holding portion 103b on cannula 104 stationary. As dilator 102 is withdrawn, cannula 104 is advanced forward to embed in the wall of the annulus approximately the distance equal to the difference in length of dilator 102 and cannula 104. Cannula 104 is secured by stabilizer 105 by unlocking the screw mechanism, sliding stabilizer 105 up against the patient's skin, and locking the screw. Probe 100 is removed once cannula 104 is secured.

Figure 23:
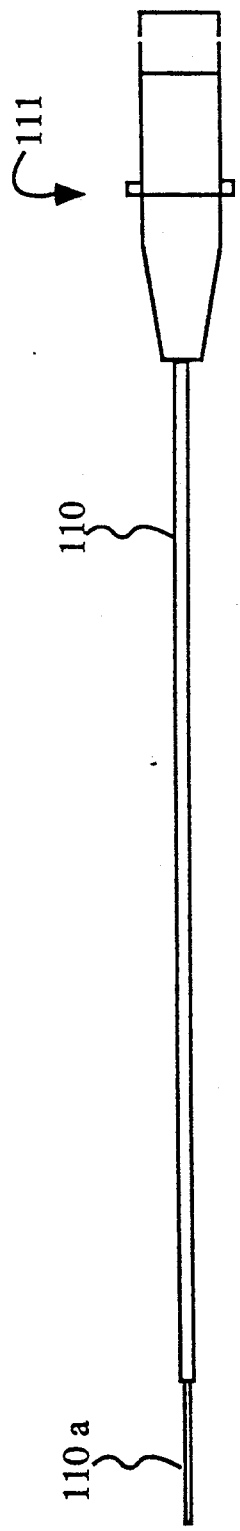
FIG. 23 is a side view illustrating an introducer means according to the present invention.

Second, one end of a first introducer means or tube 110 for inserting instrumentation according to this invention is inserted into central bore 104d at the exterior end 104b of cannula 104. First introducer means 110 is a substantially straight elongated member preferably 14 gauge along most of its length and having a 17 gauge tip 110a at one end, as illustrated in FIG. 23, and a clamping means 111 at an opposite end for clamping to an optical guiding means, as is described below. First introducer means 110 is metal, preferably type 304 stainless steel, No. 3 temper (full hard). Clamping means 111 can be plastic, preferably polycarbonate plastic or metal, preferably stainless steel. First introducer means 110 has a bore 110d (not shown) which extends through the center of first introducer means 110 along its length.

Figure 24:
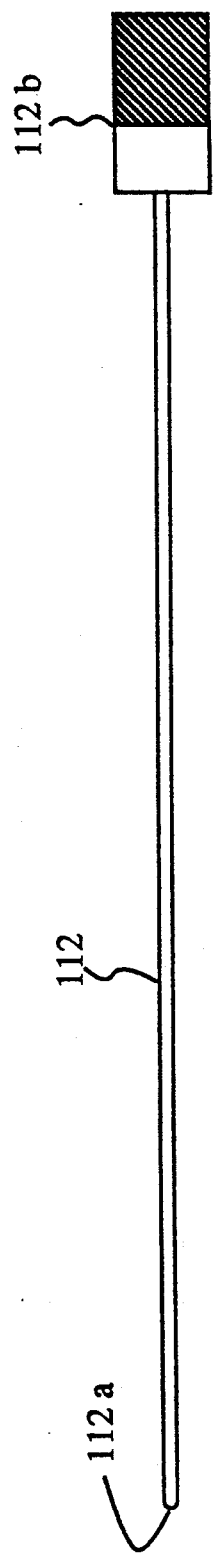
FIG. 24 is a side view illustrating a stylet used with the present invention.

When the one end 110a of first introducer means 110 is inserted into bore 104d of cannula 104, first introducer means 110 preferably has a stylet 112 extending therethrough. Stylet 112 is a long straight member, preferably 18 gauge stainless steel, having a sharp tip 112a at one end and a handle means 112b for handling stylet 112 at the opposite end, as illustrated in FIG. 24 The sharp end 112a can be a conical-shaped tip, diamond shaped tip or beveled, for example. Sharp end 112a extends out of the inserted end 110a of the first introducer means and stylet 112 locks into clamping means 111 on first introducer means 110 at handle means end 112b. The locking mechanism for clamping means 111 will be described below. Sytlet 112 is longer than and narrower in diameter than first introducer means 110 and fits within bore 110d of first introducer means 110. The clamping means 111 can also lock with handle means 112b either with a luer lock, threaded screw lock, snap lock, friction fit, but clamping means 111 is preferred.

Because the sharp tip extends out of the inserted end 110a of first introducer means 110, stylet 112 contacts the outer wall of the nucleus 18d and enters into the nucleus with its sharp tip 112a, leaving a small opening. Since the nucleus is a soft gelatinous material, stylet 112 enters the nucleus with minimal resistance and the inserted end 110a of first introducer means 110 is placed in the nucleus. Stylet 112 is removed from the nucleus through the first introducer means 110, and the first introducer means or tube 110 is left in place for introducing instrumentation into the nucleus. One end of a first optical guiding means 116 for guiding laser light is inserted through bore 110d of first introducer means after stylet 112 is removed. First optical guiding means 116 is inserted until it emanates from end 110a of first introducer means into the small opening made by stylet 112.

First optical guiding means 116 is preferably an optical fiber or a hollow optical wave guide, depending on the embodiment. In a first embodiment, the optical fiber is used which is preferably 400 micrometers in inner diameter and 600 micrometers in outer diameter and is made of quartz. In the second embodiment, the hollow optical wave guide is used which can be made from metal or ceramic and is preferably made of ceramic. The hollow waveguide is rigid compared to the optical fiber.

Figure 29:
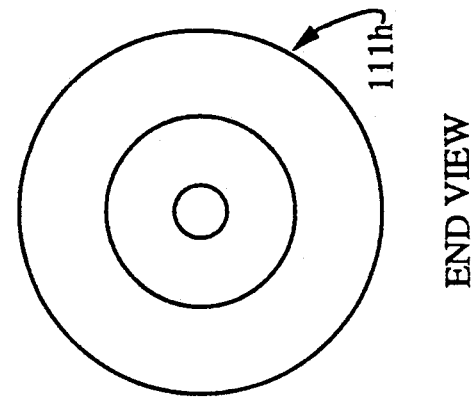
FIGS. 29A-C are sectional views illustrating a position indicator means according to the present invention.
Figure 29:
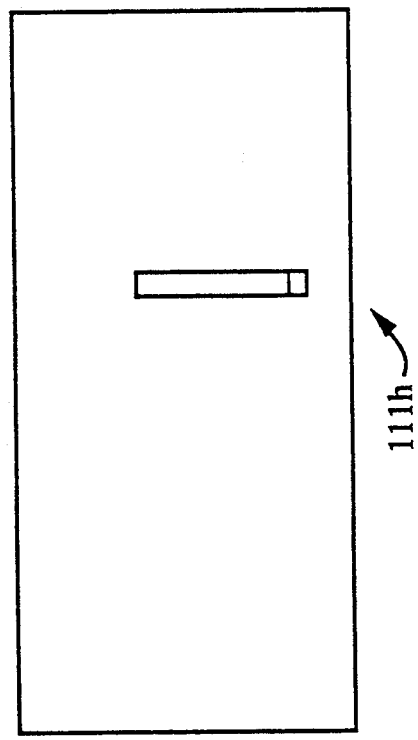
Figure 29:
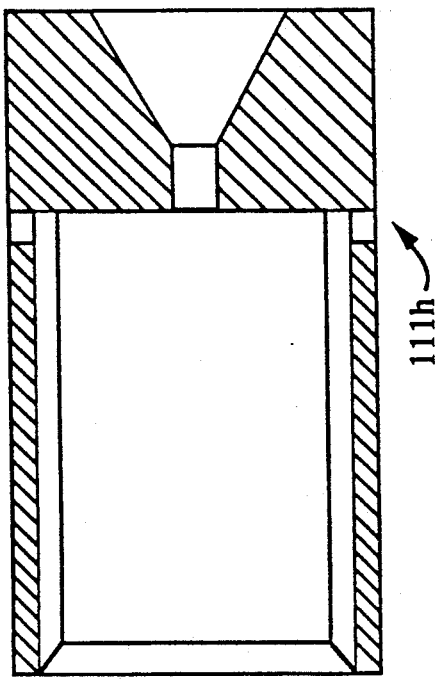

First optical guiding means 116 comprising either the optical fiber of the first embodiment or the hollow optical waveguide of the second embodiment passes through first introducer means 110 and into the nucleus 18d at a first end and is connected to a first laser means for producing laser light at a second end outside of the patient. First optical guiding means 116 preferably has a position indicator means 111h for indicating a preset distance optical guiding means 116 must extend out of first introducer means 110 at end 110a. Positioning indicator means 111h, which is described below, is illustrated in FIGS. 29A–C and serves to prevent optical guiding means 116 from being inserted beyond the preset distance by contacting clamping means 111 from one end.

Clamping means 111 then locks optical guiding means 116 in place in first introducer means 110. Clamping means 111 serves to ensure that optical guiding means 116 moves with first introducer means 110 as first introducer means 110 is manipulated during the diskectomy procedure according to the preferred embodiment.

Figure 25A:
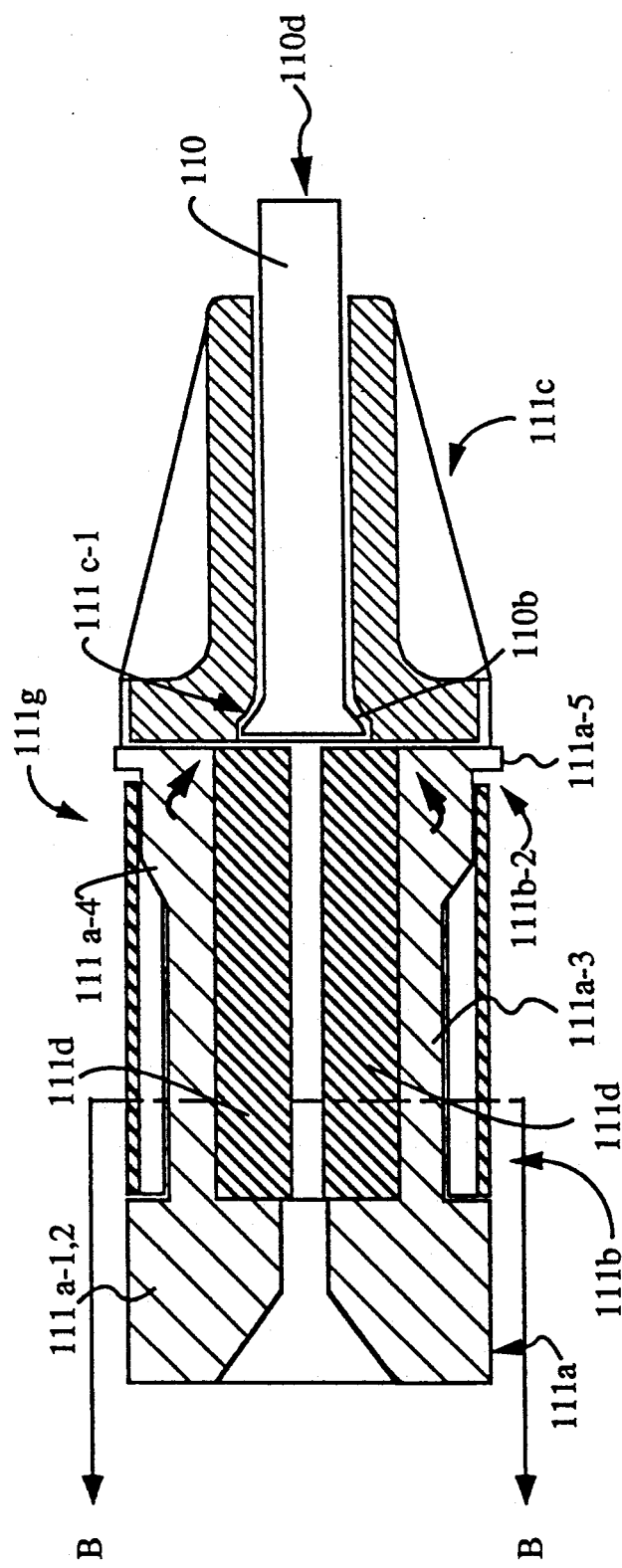
FIG. 25A-H are sectional views illustrating a clamping means according to the present invention.
Figure 25:
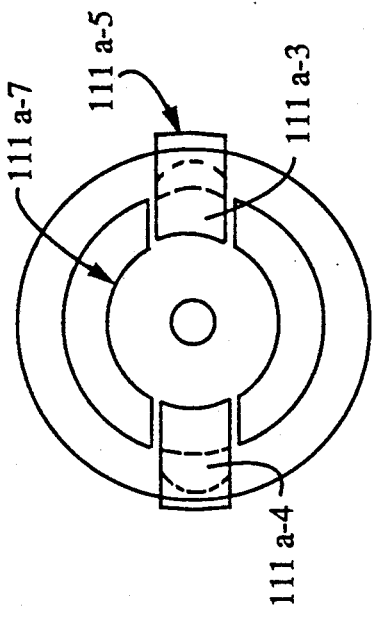
Figure 25:
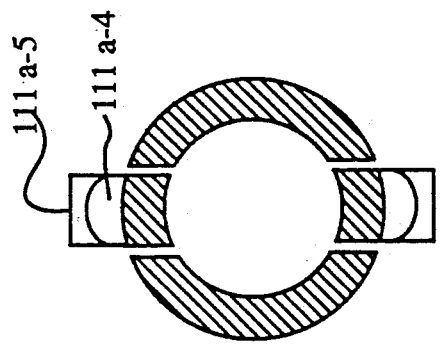
Figure 25:
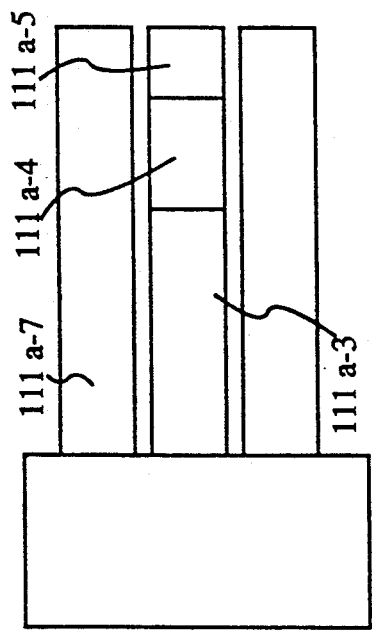
Figure 25:
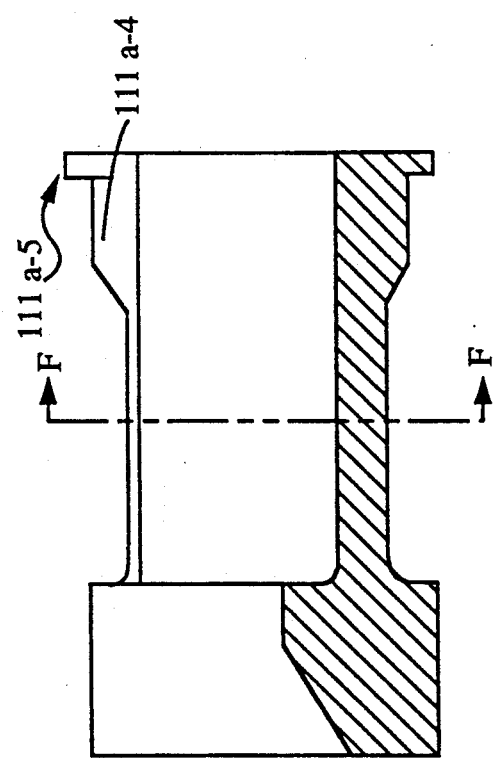
Figure 25:
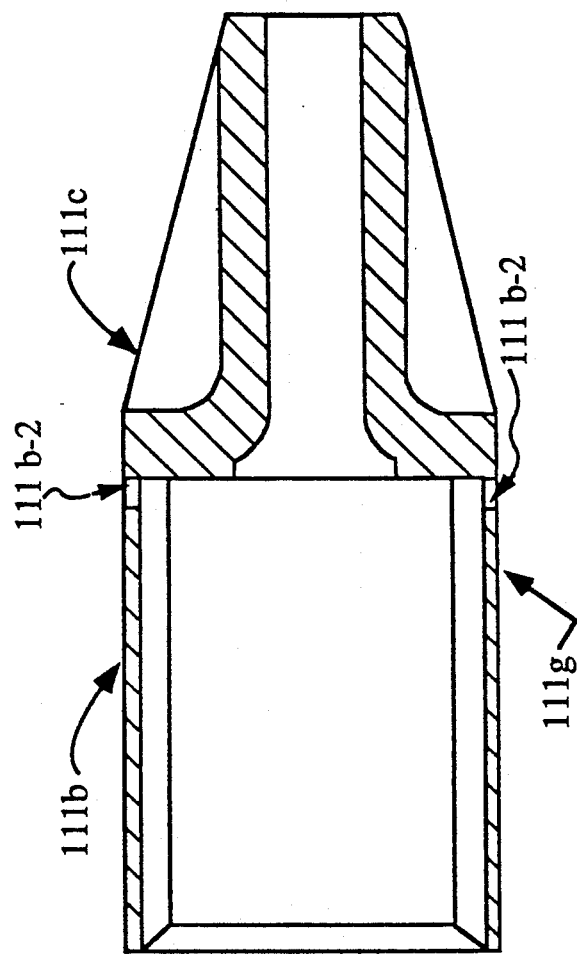
Figure 25:
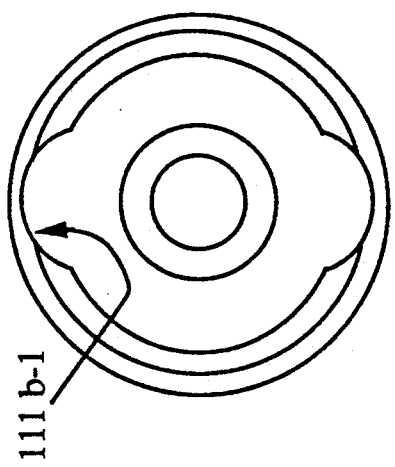

As illustrated in FIG. 25A, clamping means 111 has a clamping end 111a, midsection 111b and an introducer end 111c. Midsection 111b and introducer end 111c preferably comprise clamp housing 111g. Clamping means 111 can be made of a metal, for example stainless steel, but is preferably made of molded plastic, preferably polycarbonate plastic. Clamping end 111a comprises a clamp 111a-1 having a clamping head 111a-2, two integrally connected compression legs 111a-3, and side members 111a-7, as illustrated in FIGS. 25A–C. Side members 111a-7 are wider than compression legs 111a-3. Clamping head 111a-2, side members 111a-7, and compression legs 111a-3 are preferably molded as one piece. Legs 111a-3 and side members 111a-7 are integrally connected to head 111a-2 at one end while the opposite ends are free.

Compression legs 111a-3 and side members 111a-7 of clamp 111a-1 fit within midsection 111b of housing 111g, and each compression leg 111a-3 has a cylindrical boss 111a-4 which projects laterally therefrom, as illustrated in FIGS. 25A–F. Bosses 111a-4 fit within internal curved recesses 111b-1 of midsection 111b as illustrated in FIG. 25G when clamp 111a-1 is fully inserted into housing 111g. Curved recesses 111b-1 serve as cam surfaces while the cylindrical bosses 111a-4 serve as cam followers. Compression legs 111a-3 also each have an engagement ear 111a-5 at the free ends thereof. Engagement ears 111a-5 project laterally out and fit within retention slots 111b-2 in outer housing 111g, as illustrated in FIGS. 25A–F. Retention slots 111b-2 are located in midsection 111b near where midsection 111b and introducer end 111c meet. As clamp 111a-1 is inserted into housing 111g, bosses 111a-4 slide along recesses 111b-1 until engagement ears 111a-5 snap into retention slots 111b-2, thereby fixing the assembly together, as illustrated in FIG. 25A. Then housing 111g is rotated while clamping end 111a is held stationary, causing midsection 111b to press in on compression legs 111a-3 with cam and follower action. Engagement ears 111a-5 also move out of retention slots 111b-2 and within midsection 111b as midsection 111b is rotated.

An elastomer 111d is retained by the inner radius of compression legs 111a-3 and side members 111a-7 and is preferably tubular in shape, extending from head 111a-2 to engagement ears 111a-5, as illustrated in FIG. 25A. Elastomer 111d is a resilient material, preferably silicone rubber. Elastomer 111d grips or clamps to optical guiding means 116 when housing 111g is rotated. Optical guiding means 116 is inserted into first introducer means 110 through bore 110d to a position indicated by its position indicator means 111h, as illustrated in FIGS. 29A–C. Optical guiding means 116 is intended to extend out of end 110a for a distance, which is determined by the surgeon to be within the nucleus 18d of the afflicted disc 18b. Compression legs 111a-3 compress elastomer 111d against optical guiding means 116 in the fully rotated, locked position. The side members 111a-7 prevent radial expansion of the elastomer 111d during the compression. Elastomer 111d grips and prevents axial slippage of optical guiding means 116. The compressed elastomer 111d distributes the clamping force on the optical guiding means in such a manner that the optical transmission characteristics of optical guiding means 116 are not degraded. In addition, elastomer 111d exhibits a large coefficient of friction against optical guiding means 116. This large coefficient of friction minimizes the clamping force required to sustain a given degree of restraining force. Because of the characteristics of elastomer 111d, clamping means 111 is also removable by rotating housing 111g in the opposite direction to release the compression forces without degrading the optical guiding means 116 optical characteristics.

Both clamping means 111 and position indicator means 111h clamp and grip onto optical guiding means 116 in the same way and clamping means 111 also clamps to stylet 112 in the same fashion. The shapes of housing 111g and position indicator means (111h) differ although they comprise similar components. The differences in housing 111g and the housing 111h-1 of position indicator means 111h relate to introducer end 111c. Introducer end 111c is shaped to fit and grip end 110b of first introducer means 110. End 110b is flared as illustrated in FIG. 25A and flare grip 111c-1 holds end 110b in place. In the preferred embodiment, flared end 110b is bonded into introducer end 111c using an organic adhesive, for example fast bonding adhesives which are compatible with both plastics and metal, like cyanoacrylate adhesives. On the other hand, position indicator means 111h is shaped to facilitate the insertion of the optical guiding means 116, which does not have flared ends, as illustrated in FIGS. 29A–C.

Clamping means 111 is assembled as follows: First, end 110a of first introducer means 110 is inserted into housing 111g from midsection 111b end until flared end 110b contacts with flared grip 111c-1. End 110b of first introducer means 110 is held in place until bonded with a pre-applied adhesive Second, elastomer 111d is then inserted within the inner radius of compression legs 111a-3. Third, clamp 111a-1 is inserted into midsection 111b until engagement ears 111a-5 engage with retention slots 111b-2. Housing 111g is not rotated into the clamping position until optical guiding means 116 or stylet 112 is inserted and clamping is necessary.

Fourth, using laser energy from the laser means through first optical guiding means 116, some of the nucleus pulposus within nucleus 18d is vaporized to create a first vaporized area in the nucleus 18d of the herniated disc 18b. The first vaporized area provides a space or cavity in the nucleus pulposus into which nucleus pulposus from the herniated area 18c can fill and thereby contract away from nerve root 18e. First optical guiding means 116 along with first introducer means 110 are removed from cannula 104 when the vaporization step is complete.

According to the invention, a second vaporization step is included. According to the preferred embodiment, a second introducer means 130 is inserted into cannula 104 to contact the first vaporized area.

Figure 26:
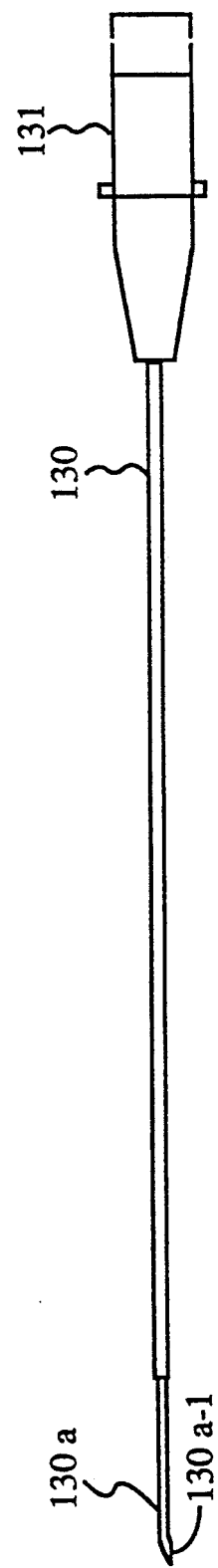
FIG. 26 is a side view illustrating an introducer means having a formed end according to the present invention.

Second introducer means 130 is preferably 14 gauge along its length and has a 17 gauge tip 130a. Second introducer means 130 is metal, preferably type 304 stainless steel, No. 3 temper (full hard). Moreover, the opening in tip 130a of second introducer means 130 is formed differently from first introducer means 110, as illustrated in FIG. 26 and in an exploded view illustrated in FIG. 27. Rather than opening 130a-1 being perpendicular to the longitudinal axis of the tubular member as is shown for first introducer means, opening 130a-1 at end 130a is curved relative to the longitudinal axis. Curved end 130a is not flared out nor wider than the 14 gauge portion of the tubular member. As a result, curved end 130a of second introducer means 130 need not be wider in diameter than first introducer means 110. In the preferred embodiment, second introducer means 130 is the same inner and outer diameter as first introducer means 110 and has a curvature at end 130a within that outer diameter. Therefore, second introducer means 130 fits within cannula 104 in the same way first introducer means 110 fits within cannula 104. Cannula 104 remains in the patient's body to receive second introducer means 130 for the second vaporization step according to the preferred embodiment, as described below.

The curved end 130a of second introducer means 130 enters the nucleus 18d and contacts the first vaporized area when second introducer means 130 is inserted into cannula 104. One end of a second optical guiding means 132 is inserted through a central bore 130d, of second introducer means 130 to emanate from opening 130a-1 into the first vaporized area at the formed end 130a of second introducer means 130, as illustrated in the exploded view in FIG. 27. Second optical guiding means 132 has a position indicator means which is the same as position indicator means 111h on first optical guiding means 116. The position indicator means on second optical guiding means 132 contacts with clamping means 131 in the same way as described above for first introducer 110 means and position indicator means 111h. Clamping means 131 and 111 are essentially the same and clamping means 131 is illustrated in FIG. 26. When end 132a of second optical guiding means 132 emanates from opening 130a-1 of curved end 130a on second introducer means 132, end 132a of second optical guiding means 132 is deflected off the longitudinal axis of the second optical guiding means 132.

The amount which second optical guiding means 132 is deflected is dependent upon the radius of curvature of end 130a of second introducer means 130. The considerations made when determining what radius of curvature to use at least depended on several factors, according to the invention. First, the minimum radius of curvature should be so formed at the tip of an introducer means so that the curved introducer means still fits within cannula 104. Second, optical guiding means 116 or 132, for example an optical fiber, should deflect with uniform curvature to achieve a minimal loss of laser light guiding efficiency. Third, the radius of curvature of the introducer means allowable and the diameter of the optical guiding means allowable are mutually dependent. According to the preferred embodiment, the radius of curvature is 0.45 which deflects second optical guiding means 132 about 17° from the longitudinal axis when second optical guiding means 132 is a 400 μm optical fiber. Second optical guiding means 132 can be deflected between the range of 1° to 30° by curved end 130a of second introducer means 130, for the preferred embodiment.

Once second optical guiding means 132 is in place and positioned so that it extends out of curved end 130a of second introducer means 130 for a distance, as predetermined by the surgeon, optical guiding means 132 is locked in place by clamping means 131 in much the same way as described previously for clamping means 111. Therefore, clamping of second optical guiding means 132 to second introducer means 130 allows second optical guiding means to be manipulated as second introducer means 130 is manipulated. An end of second optical guiding means 132 opposite to the deflected end is attached to a second laser means. Light energy from the second laser means is guided by second optical guiding means 132 into the nucleus 18d to vaporize nucleus pulposus and create a second vaporized area within nucleus 18d. The second vaporized area 145 of the preferred embodiment is larger than the first vaporized area and the larger area is created by the deflected beam emanating from deflected end 132a of second optical guiding means 132 during this vaporization step. Manipulation of second introducer means 130 with second optical guiding means 132 clamped thereto will cause manipulation of the deflected beam as well.

Figure 30:
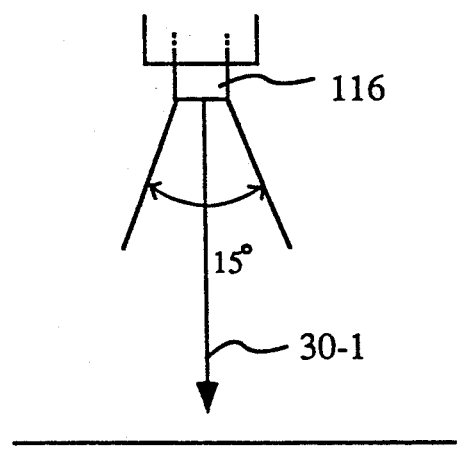
FIGS. 30A,B are plan views illustrating the first line of a laser beam.
Figure 30:
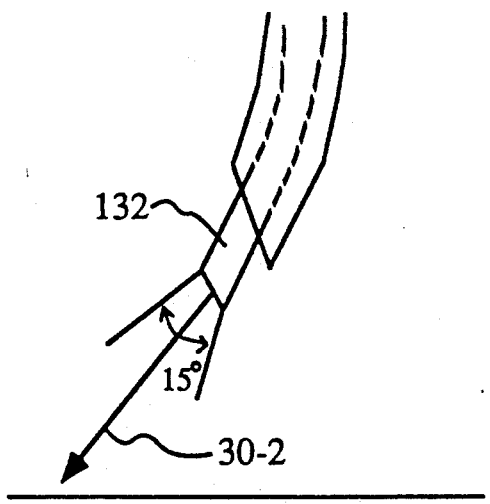

According to the invention, when the laser beam is applied generally along a line 30-1 to a herniated disc area, the line or path that the laser beam takes is illustrated by example in FIG. 30A. Line 30-1 is obtained by moving first introducer means 110 having first optical guiding means 116 disposed therethrough axially within cannula 104. Since laser beams according to the invention are divergent and emanate in a 15° cone from the guiding means, the line or path defined by the divergent beam is described as a single overall direction the laser beam travels, as illustrated by arrow A in FIG. 30A. Line 30-2 to a herniated disc area can also be the path of the laser beam, as illustrated in FIG. 30B. Line 30-2 to a herniated disc area is obtained with second introducer means 130 having second optical guiding means 132 disposed therethrough, being deflected off the longitudinal axis by curved end 130a. The laser beam guided through deflected second optical guiding means 132 is applied along line 30-2.

Figure 31:
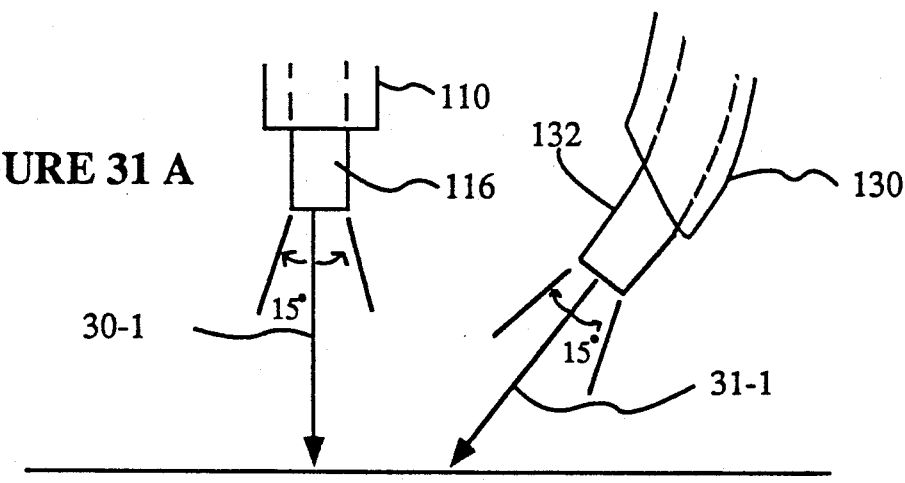
FIGS. 31A-C are plan views illustrating the second line of a laser beam.
Figure 31:
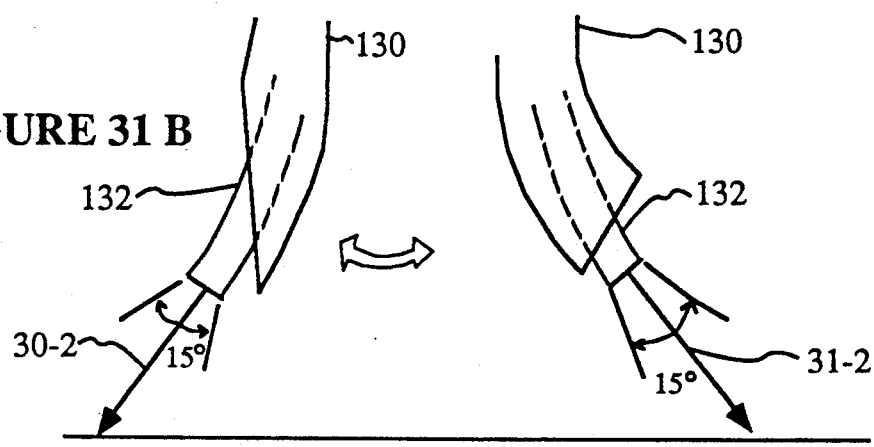
Figure 31:
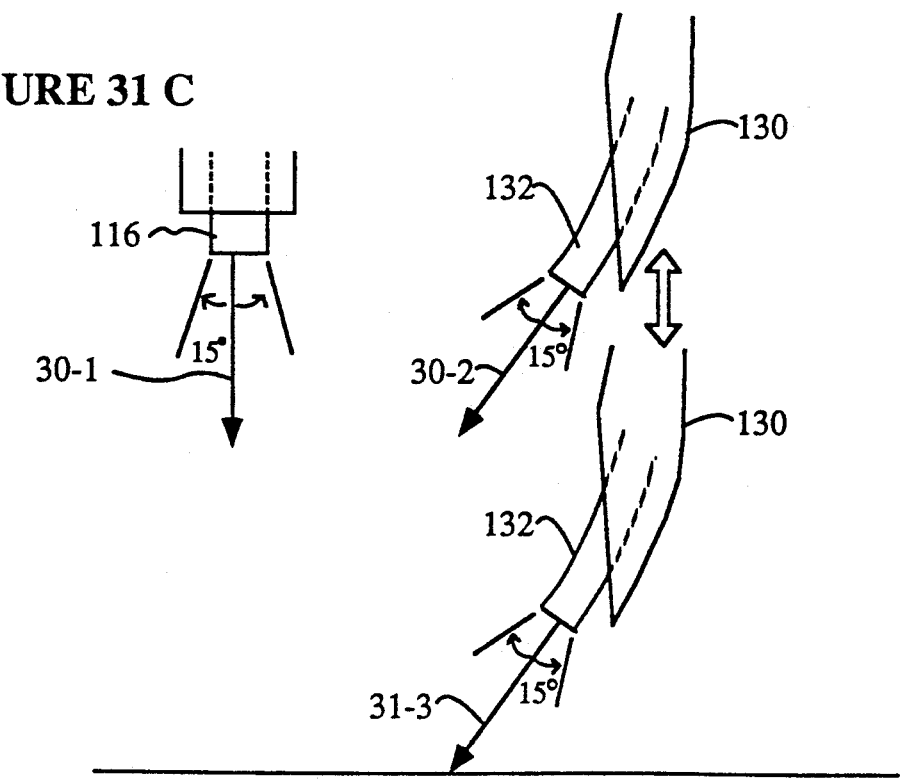

The laser beam can be applied along a line 31-1, as illustrated in FIG. 31A. Line 31-1 is different from line 30-1, as illustrated in FIGS. 30A and 31A and the difference is at least due to shape of straight first introducer means 110 relative to the shape of curved second introducer means 130. Line 31-1 is obtained by guiding a laser beam along second optical guiding means 132 while second optical guiding means 132 is disposed in curved second introducer means 130.

When the laser beam is applied along line 31-2, line 31-2 is different from line 30-1 and line 30-2, as illustrated in FIGS. 31A and 31B. Line 31-2 is obtained by guiding a laser beam along second optical guiding means 132 while second optical guiding means is disposed in curved second introducer means 130. Moreover, curved end 130a of second introducer means 130 is inserted into cannula 104 at a position rotated a distance from line 30-2. Line 31-2 is at an angle to both line 30-1 and line 30-2.

When the laser beam is applied along a line 31-3, line 31-3 is different from line 30-1 and line 30-2, as illustrated in FIG. 31C. Line 31-3 is at an angle to line 30-1 and parallel to line 30-2. Line 31-3 is obtained by guiding a laser beam along second optical guiding means 132 while second optical guiding means 132 is disposed in curved second introducer means 130 and second introducer means 130 is moved axially a distance within cannula 104 along the path followed by second introducer means 130 for line 30-2.

According to the preferred embodiment, second introducer means 130 having curved tip 130a can be moved axially within cannula 104 while the laser beam applied to the nucleus from deflected end 132a of second optical guiding means is at an angle to the direction of movement. Moreover, second introducer means 130 having second optical guiding means 132 disposed therethrough can be rotated to any distance through 360° to apply the laser beam in an arc up to 360°. The laser beam from second introducer means 130 can be applied along a plurality of lines through 360° or less and each line would be at an angle to the previous line. Second introducer means 130 can be moved axially within cannula 104 while being rotated through 360 degrees at least one time and preferably several times during the second vaporization step. The deflected beam from second optical guiding means 132 and the movement increase the amount of nucleus pulposus vaporized in second vaporized area 145. Second introducer means 130 having curved end 130a articulates second optical guiding means 132 to increase the amount of nucleus pulposus which can be vaporized. Second introducer means 130 articulates the second optical guiding means 132 in a static way because second introducer means 130 has one predetermined curved end 130a which will deflect second optical guiding means 132 in one way and to only one degree. Different optical guiding means having different radii of curvature can be used in addition to second introducer means 130 and still be within the scope of the invention. On the other hand, variable articulators are known in the art which articulate optical fibers in numerous ways and to different degrees in endoscopic procedures. Variable or dynamic articulators of the relevant art are much larger in diameter and require much larger paths in which they are manipulated. As a result, variable articulators are used in endoscopic surgery through preexisting body cavities. Second introducer means 130 is a static articulator which can be manipulated within much smaller paths than the variable articulators because of second introducer means 130 design and construction. Therefore, static articulator or second introducer means 130 of the present invention works well in percutaneous procedures while variable articulators do not. Also, second introducer means 130 can vaporize a larger given area than straight first introducer means 110 when each is manipulated along the same small path or cannula 104, as described above.

Second optical guiding means 132 can be of the same construction as first optical guiding means 116 or can be different. In the preferred embodiment, second optical guiding means 132 is the same construction as the first optical guiding means, and in particular, can be the same optical guiding means used for optical guiding means 116. In the first embodiment, an optical fiber is used as first optical guiding means 116. Optical fiber 117 can be used as second optical guiding means 132 or another optical fiber can be used. The optical fibers 117a can have the same construction or can be different. The optical fibers are preferably the same construction. The optical fibers can be multiuse (reusable) or single use (disposable). In the second embodiment, the hollow optical waveguide is used as first optical guiding means 110. A hollow optical waveguide can be used as second optical guiding means 132, as well, with slight modification to one end of the optical waveguide to adapt it to formed end 130a of second introducer means 130. Nevertheless, the optical fibers of the first embodiment are preferred over the hollow optical waveguides for the present invention. Alternatively, one optical guiding means can be an optical fiber, while the other optical guiding means can be an optical wave guide in a third embodiment. The particular optical guiding means used for the different embodiments will depend on the laser means which is also used.

First and second laser means can be the same laser or two different lasers may be used to produce a laser beam for vaporizing nucleus pulposus. According to the present invention, only one laser is necessary. The laser system used for percutaneous diskectomy according to the present invention can emit energy in the temporal continuous mode or pulse mode in the ultraviolet, visible and infrared ranges of the electromagnetic spectrum. Table I lists the lasers and the associated wavelengths for use in percutaneous diskectomies according to the invention. For example, a Nd:YAG laser which emits energy at 1064 nm can be modified by second harmonic generation to create a laser beam at another wavelength. In the preferred embodiment, a Nd:YAG laser which emits light at 1064 nm is coupled with a frequency doubler to generate a laser beam at 532 nm. For the preferred embodiment, a solid state media is used as a frequency doubler, in particular a potassium, titanyl phosphate crystal (KTP), to create a laser system according to the present invention which is usable with either laser means or both. The laser system of the preferred embodiment, has been used for other percutaneous surgical procedures in the areas of gynecology, urology, dermatology, gasteroenterology, otorhinolaryngology, and other neurosurgeries, but has not been used for applying a laser beam in percutaneous diskectomies, according to the present invention. The laser system of the preferred embodiment is known in the art as KTP/532 TM Surgical Laser System.

TABLE I

LIST OF LASERS FOR USE IN PERCUTANEOUS DISKECTOMY

| Laser Type | Wavelength (Nanometers or Micrometers) |
|---|---|
| CO$_2$ | 10.6 μm |
| CO | 5, 7 μm |
| Erbium: YAG | 2.94 μm |
| Holmium: YAG | 1950 nm, 2150 nm |
| Krypton | 647 nm |
| Argon | 488 nm, 514.5 nm |
| Dye Lasers | 350 nm, 1000 nm |
| Nd: YAG | 1320 nm |
| Nd: YAG (frequency doubled) | 532 nm, 660 nm |
| Nd: YAG (frequency tripled) | 354.7 nm, 440 nm |
| Nd: YAG (frequency quadrupled) | 266 nm, 330 nm |
| Tunable Lasers: | |
| Co:MgF$_2$ | 1.75 μm, 2.5 μm |
| Ti: Sapphire | 660 nm, 990 nm |
| Ti: Sapphire (frequency doubled) | 330 nm, 495 nm |
| Alexandrite | 730 nm, 780 nm |
| Alexandrite (frequency doubled) | 365 nm, 390 nm |
| Excimer Lasers: | |
| Xenon Chloride | 308 nm |
| Xenon Fluoride | 248 nm |
| Argon Fluoride | 193 nm |
| Krypton Fluoride | 248 nm |

The laser system according to the present invention should be any laser which emits laser energy that is absorbed by body tissue. The laser means is are preferably one laser system which is used in both the first and second vaporization steps.

Any laser system used in accordance with the present invention that emits a laser beam in the ultraviolet or visible range of the electromagnetic spectrum can be used in conjunction with optical guiding means 116 and 132 of the first embodiment, namely an optical fiber. Any laser system that emits a laser beam in the infrared range of the electromagnetic spectrum can be used in conjunction with optical guiding means 116 and 132 of the second embodiment, namely a hollow optical waveguide 118 or 118a. Therefore, the Argon laser for example, or preferably Nd:YAG laser modified by second harmonic generation will emit a laser beam that is conducted by an optical fiber, according to the present invention. The $CO_2$ laser will emit a laser beam that is conducted by a hollow optical waveguide, according to the present invention. In the third embodiment, two lasers are used, one laser which typically uses an optical fiber to conduct its laser beam and one laser which typically uses a hollow optical waveguide to conduct its laser beam, as described above.

After the second vaporization step according to the preferred embodiment, second optical guiding means 132 and second introducer means 130 are removed from cannula 104. In the preferred embodiment, cannula 104 is also removed and the entry point through the skin is covered with a sterile bandage. The patient is then allowed to leave the hospital and recuperate at home under minimal restrictions or requirements.

Figure 28:
FIG. 28 is a side view of an irrigation/aspiration cannula used with the present invention.

Alternatively, in a fourth embodiment an irrigation/aspiration cannula 150, is inserted into cannula 104 after second introducer means 130 and second optical guiding means 132 are removed. Irrigation/aspiration cannula 150 is preferably 15 gauge along its length and has a 17 gauge tip 150a, as illustrated in FIG. 28. Cannula 150 is used to evacuate the second vaporization area so that second vaporization area can be further cleansed in the unlikely event that loose fragments or debris might be present. A vacuum suction device is attached to end 150a of cannula 150 and the area is aspirated, before cannula 104 is removed.

The means for inserting instrumentation necessary for percutaneous diskectomy using a laser can be packaged in a kit and sold, for example, for single use or multiple use. The kit may contain probe 100, straight cannula 104, curved cannula 106, first introducer means 110, second introducer means 130, stylet 112, cannula 150 and tools such as a marking pen, scalpel with blade, measuring scale and a locking stabilizer 105. The kit may contain all these items or some of them. Furthermore, optical guiding means 116 and 132 may be included. The laser system according to the preferred and exemplary embodiments may be supplied separately.

While the invention has been described in connection with several exemplary embodiments, it will be understood that many modifications will be apparent to those of ordinary skill in the art, while still being within the intended scope of the present invention.

What is claimed is:

1. A method of performing percutaneous diskectomy using a laser comprising applying a laser beam to a herniated disk having a nucleus while deflecting the laser beam away from a longitudinal axis of the laser beam in the nucleus of the disk, said laser beam having a wavelength in the range of 350 nanometers through 1,000 nanometers.

2. A method of performing percutaneous diskectomy according to claim 1, wherein the wavelength is 647 nanometers.

3. A method of performing percutaneous diskectomy according to claim 1 wherein the wavelength is 488 nanometers.

4. A method of performing percutaneous diskectomy according to claim 1 wherein the wavelength is 532 nanometers.

5. A method of performing percutaneous diskectomy according to claim 1 wherein the wavelength is 354.7 nanometers.

6. A method of performing percutaneous diskectomy according to claim 1 wherein the wavelength is 440 nanometers.

7. A method of performing percutaneous diskectomy according to claim 1 wherein the wavelength is 990 nanometers.

8. A method of performing percutaneous diskectomy according to claim 1 wherein the wavelength is 495 nanometers.

9. A method of performing percutaneous diskectomy according to claim 1 wherein the wavelength is 730 nanometers.

10. A method of performing percutaneous diskectomy according to claim 1 wherein the wavelength is 780 nanometers.

11. A method of performing percutaneous diskectomy according to claim 1 wherein the wavelength is 365 nanometers.

12. A method of performing percutaneous diskectomy according to claim 1 wherein the wavelength is 390 nanometers.

13. A method of performing percutaneous diskectomy comprising applying a laser beam to a herniated disk having a nucleus while deflecting the laser beam away from a longitudinal axis of the leaser beam in the nucleus of the disk, said laser beam having a wavelength of 5 microns.

14. A method of performing percutaneous diskectomy comprising applying a laser beam to a herniated disk having a nucleus while deflecting the laser beam away from a longitudinal axis of the laser beam in the nucleus of the disk, said laser beam having a wavelength of 7 microns.

15. A method of performing percutaneous diskectomy comprising applying laser beam to a herniated disk having a nucleus while deflecting the laser beam away from a longitudinal axis of the laser beam in the nucleus of the disk, said laser beam having a wavelength of 1950 nanometers.

16. A method of performing percutaneous diskectomy comprising applying a laser beam to a herniated disk having a nucleus while deflecting the laser beam away from a longitudinal axis of the laser beam in the nucleus of the disk, said laser beam having a wavelength of 2115 nanometers.

17. A method of performing percutaneous diskectomy comprising applying a laser beam to a herniated disk having a nucleus while deflecting the laser beam away from a longitudinal axis of the laser beam in the nucleus of the disk, said laser beam having a wavelength of 1.75 microns.

18. A method of performing percutaneous diskectomy comprising applying a laser beam to a herniated disk having a nucleus while deflecting the laser beam away from a longitudinal axis of the laser beam in the nucleus of the disk, said laser beam having a wavelength of 2.5 microns.

19. A method of performing percutaneous diskectomy comprising applying a laser beam to a herniated disk having a nucleus while deflecting the laser beam away from a longitudinal axis of the laser beam in the nucleus of the disk, said laser beam having a wavelength of 10.6 microns.

20. A method of performing percutaneous diskectomy comprising applying a laser beam to a herniated disk having a nucleus while deflecting the laser beam away from a longitudinal axis of the laser beam in the nucleus of the disk, said laser beam having a wavelength of 2.94 microns.

21. A method of performing percutaneous diskectomy comprising applying a laser beam to a herniated disk having a nucleus while deflecting the laser beam away from a longitudinal axis of the laser beam in the nucleus of the disk, said laser beam having a wavelength of 1320 nanometers.

22. A method of performing percutaneous diskectomy comprising applying a laser beam to a herniated disk having a nucleus while deflecting the laser beam away from a longitudinal axis of the laser beam in the nucleus of the disk, said laser beam having a wavelength of 330 nanometers.

23. A method of performing percutaneous diskectomy comprising applying a laser beam to a herniated disk having a nucleus while deflecting the laser beam away from a longitudinal axis of the laser beam in the nucleus of the disk, said laser beam having a wavelength of 308 nanometers.

24. A method of performing percutaneous diskectomy comprising applying a laser beam to a herniated disk having a nucleus while deflecting the laser beam away from a longitudinal axis of the laser beam in the nucleus of the disk, said laser beam having a wavelength of 266 nanometers.

25. A method of performing percutaneous diskectomy comprising applying a laser beam to a herniated disk having a nucleus while deflecting the laser beam away from a longitudinal axis of the laser beam in the nucleus of the disk, said laser beam having a wavelength of 2150 nanometers.

26. A method of performing percutaneous dickectomy comprising applying a laser beam to a herniated disk, having a nucleus, while deflecting the laser beam away from a longitudinal axis of the laser beam in the nucleus of the disk, said laser beam having a wavelength of 249 nanometers.

27. A method of performing percutaneous dickectomy comprising applying a laser beam to a herniated disk, having a nucleus, while deflecting the laser beam away from a longitudinal axis of the laser beam in the nucleus of the disk, said laser beam having a wavelength of 193 nanometers.

28. A method of performing percutaneous dickectomy comprising applying a laser beam to a herniated disk, having a nucleus, while deflecting the laser beam away from a longitudinal axis of the laser beam in the nucleus of the disk, said laser beam having a wavelength of 248 nanometers.

29. A method of performing percutaneous diskectomy comprising applying a laser beam to a herniated disk having a nucleus while deflecting the laser beam away from a longitudinal axis of the laser beam in the nucleus of the disk, said laser beam having a wavelength of 514.5 nanometers.

* * * * *